(12) United States Patent
Fong et al.

(10) Patent No.: US 9,046,529 B2
(45) Date of Patent: Jun. 2, 2015

(54) PROSTATITIS-ASSOCIATED ANTIGENS AND METHODS OF USE THEREOF

(75) Inventors: Lawrence H. Fong, Palo Alto, CA (US); Yafei Hou, Mountain View, CA (US); Jason J. Devoss, San Francisco, CA (US); Mark Stuart Anderson, Larkspur, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 13/262,752

(22) PCT Filed: Mar. 30, 2010

(86) PCT No.: PCT/US2010/029174
§ 371 (c)(1),
(2), (4) Date: Dec. 2, 2011

(87) PCT Pub. No.: WO2010/117768
PCT Pub. Date: Oct. 14, 2010

(65) Prior Publication Data
US 2012/0093820 A1   Apr. 19, 2012

Related U.S. Application Data

(60) Provisional application No. 61/168,506, filed on Apr. 10, 2009.

(51) Int. Cl.
| | | |
|---|---|---|
| *G01N 33/68* | (2006.01) | |
| *C07K 14/47* | (2006.01) | |
| *A61K 39/00* | (2006.01) | |

(52) U.S. Cl.
CPC .......... *G01N 33/6893* (2013.01); *A61K 39/00* (2013.01); *C07K 14/47* (2013.01); *G01N 2800/342* (2013.01)

(58) Field of Classification Search
CPC .................................................. A61K 39/00
See application file for complete search history.

(56) References Cited

U.S. PATENT DOCUMENTS

| | | |
|---|---|---|
| 2001/0007748 A1 | 7/2001 | An et al. |
| 2008/0268463 A1 | 10/2008 | Dimitrakov et al. |
| 2009/0060842 A1 | 3/2009 | Fehre et al. |

FOREIGN PATENT DOCUMENTS

WO   WO 96/00503   1/1996

OTHER PUBLICATIONS

Alexander et al (Urology, 1997, 50(6): 893-899).*
Lilja et al (JBC, 1989, 264(3): 1894-1900).*
Tockman et al (Cancer Res., 1992, 52:2711s-2718s).*
Dunphy et al (J Clin Immunol, 2004, 24(5): 492-502).*
Koistinen et al (Biol Reprod, 2002, 66(3): 624-628).*
Yoshida et al (Journal of Andrology, 2003, 24(6): 878-884).*
Zhang et al (J Immunother, 2003, 26(6): 461-467).*
Torn et al (Diabetes Metab Res Rev, 2000, 16: 442-447).*
Batstone, et al., "Autoimmune T Cell Responses to Seminal Plasma in Chronic Pelvic Pain Syndrome (CPPS)", 2002, Clin. Exp. Immunol., vol. 128, No. 2, pp. 302-307.
Bernstein, et al., "Medically Significant Concentrations of Prostate-Specific Antigen in Serum Assessed", 1990, vol. 36, No. 3, pp. 515-518.
Hou, et al., "An Aberrant Prostrate Antigen-Specific Immune Response Causes Prostatitis in Mice and is Associated with Chronic Prostatitis in Humans", 2009, J. Clin. Invest., vol. 119, No. 7, pp. 2031-2041.
Lundwall, et al., "A Novel Gene Family Encoding Proteins with Highly Differing Structure Because of a Rapidly Evolving Exon", 1995, FEBS Letters, vol. 374, pp. 53-56.
Motrich, et al., "Autoimmune Prostatitis: State of the Art", 2007, Scand. Immunol., vol. 66, No. 2-3, pp. 217-227.

* cited by examiner

*Primary Examiner* — Sean Aeder
(74) *Attorney, Agent, or Firm* — Bozicevic, Field & Francis LLP; Paula A. Borden

(57) ABSTRACT

The present disclosure provides prostatitis-associated antigens, and compositions comprising the antigens. The present disclosure provides diagnostic methods, generally involving assaying the level of an immune response specific for a prostatitis-associated antigen in an individual. Kits suitable for use in performing such diagnostic assays are also provided. The present disclosure further provides methods of treating prostatitis, methods of treating prostate cancer, and methods of treating benign prostatic hyperplasia.

5 Claims, 12 Drawing Sheets

Semenogelin I (isoform a) (SEQ ID NO: 1)
MKPNIIFVLSLLLILEKQAAVMGQKGGSKGRLPSEFSQFPHGQKGQHYSGQKGQHYSGQKGKQQTESKGSFSIQ
YTYHVDANDHDQSRKSQQYDLNALHKTTKSQRHLGSGQLLHNKQEGRDHDKSKGHFHRVVIH
HKGGKAHRGTQNPSQDQGNSPSGKGISSQYSNTEERLWVHGLSKEQTSVSGAQKGRKQGGSQSS
YVLQTEELVANKQQRETKNSHQNKGHYQNVVEVREEHSSKVQTSLCPAHQDKLQHGSKDIFSTQ
DELLVYNKNQHQTKNLNQDQQHGRKANKISYQSSSTEERRLHYGENGVQKDVSQSSIYSQTEEK
AQGKSQKQITIPSQEQEHSQKANKISYQSSSTEERRLHYGENGVQKDVSQRSIYSQTEKLVAGKSQI
QAPNPKQEPWHGENAKGESGQSTNREQDLLSHEQKGRHQHGSHGGLDIVIIEQEDDSDRHLAQHL
NNDRNPLFT

FIG. 9A

Semenogelin I (isoform b) (SEQ ID NO: 2)
MKPNIIFVLSLLLILEKQAAVMGQKGGSKGRLPSEFSQFPHGQKGQHYSGQKGKQQTESKGSFSIQ
YTYHVDANDHDQSRKSQQYDLNALHKTTKSQRHLGSGQLLHNKQEGRDHDKSKGHFHRVVIH
HKGGKAHRGTQNPSQDQGNSPSGKGISSQYSNTEERLWVHGLSKEQTSVSGAQKGRKQGGSQSS
YVLQTEELVANKQQRETKNSHQNKGHYQNVVEVREEHSSKVQTSLCPAHQDKLQHGSKDIFSTQ
DELLVYNKNQHQTKNLNQDQQHGRKANKISYQSSSTEERRLHYGENGVQKDVSQRSIYSQTEKL
VAGKSQIQAPNPKQEPWHGENAKGESGQSTNREQDLLSHEQKGRHQHGSHGGLDIVIIEQEDDSD
RHLAQHLNNDRNPLFT

FIG. 9B

Semenogelin II (SEQ ID NO: 3)
MKSIILFVLSLLLILEKQAAVMGQKGGSKGQLPSGSSQFPHGQKQHYFGQKDQHTKSKGSFSIQ
HTYHVDINDHDWTRKSQQYDLNALHKATKSKQHLGGSQLLNYKQEGRDHDKSKGHFHMIVIH
HKGGQAHHGTQNPSQDQGNSPSGKGLSSQCSNTEKRLWVHGLSKEQASASGAQKGRTQGGSQSS
YVIQTEELVVNKQRETKNSHQNKGHYQNVVDVREEHSSKLQTSLHPAHQDRLQHGPKDIFTTQ
DELLVYNKQHQTKNLSQDQEHGRKAHKISYPSSRTEERQLHHGEKSVQKDVSKGSISIQTEEKIH
GKSQNQVTIHSQDQEHGHKENKISYQSSSTEERHLNCGEKGHQKGVSKGISIQTEEQIHGKSQNQV
RIPSQAQEYGHKENKISYQSSSTEERRLNSGEKDVQKGVSKGSISIQTEEKHHGKSQNQVTIPSQDQE
HGHKENKMSYQSSSTEERRLNYGGKSTQKDVSQSSISFQIEKLVEGKSQIQTPNPNQDQWSGQNA
KGKSGQSADSKQDLLSH EQKGRYKQESSESHNIVITHEVAQDDHLTQQYNEDRNPIST

FIG. 9C

SVS2 (MOUSE) (SEQ ID NO: 4)
MKSSVFVLSLLLILERQSAVFVQYCATKGHFQSSSSEGFMLGQKCRLSFQIKGGSDEAAEESLFMQ
SQRRVYGQGGDMTQTRVSQEHTSVKGAALCRNGQVSQLKSQESQIKSYGQVKSSGQLKSSGSA
FQQVKSSVSQIKSYGQLKSGGPAFGQVKSQESQIKSYGQLKSSGQLKSGGSAFGQVKSSV
SQIKSYGQLKSGGSQVKSYGQTKSYGEEGQLNSFSQLKSGAQLKSYGQQKSQQQSFSQVKSQS
SQLKSYGQQKSLKGFSQNTQHKGFAMIDEGMSQVRKQFSIDDDLSVQQKSTQQMKTEEDLSQFGQ
QRQYGQGQERSQSYKGYLEQYRKKVQEQQRKNFNPGNYFTKGGADLYQAQLKG

FIG. 9D

SVS2 (RAT) (SEQ ID NO: 5)
MKSSVFIILSLFLLLERQAAVVGQYGGTKGHFQSSSSGFMLGQKGHLNFGLKGGSEEAAEESIFMQS
QHQMFCQDGGDMAQTSVSQEHTGVKGAAICRKGQVSQLKSQESQIKSFRQVKSSGQLKSGGSQL
KSFGQVKSSESQLKSFGQVKASGSQLKSFGQVKASGSQLKSYGQMKSSGSQVKSFGQMKSSGSQV
KSFGQMKASESQIKSFGQRKSQGGQLQSYGQMKSYGQTKSLESQAKSFGQVKSQSGQMKSSYGQ
RKSYGEETQLKSFDQBAQLKSYGQKSQKQSSFSQVKSQSAQLKSFGQQKSLKGFSQQTQKGFA
MDEDLSQVRKQFDDDLSVQQKSTQQMKTEEDLSQFGQQRQFGQERSQSYKGYLAQYRKKLQE
QQQKNFNQDNFFTKGGAGLYQAQLKG

FIG. 9E

SEQUENCE LISTING

```
<160> NUMBER OF SEQ ID NOS: 5

<210> SEQ ID NO 1
<211> LENGTH: 462
<212> TYPE: PRT
<213> ORGANISM: Homo sapiens

<400> SEQUENCE: 1

Met Lys Pro Asn Ile Ile Phe Val Leu Ser Leu Leu Leu Ile Leu Glu
1               5                   10                  15

Lys Gln Ala Ala Val Met Gly Gln Lys Gly Gly Ser Lys Gly Arg Leu
            20                  25                  30

Pro Ser Glu Phe Ser Gln Phe Pro His Gly Gln Lys Gly Gln His Tyr
        35                  40                  45

Ser Gly Gln Lys Gly Lys Gln Gln Thr Glu Ser Lys Gly Ser Phe Ser
    50                  55                  60

Ile Gln Tyr Thr Tyr His Val Asp Ala Asn Asp His Asp Gln Ser Arg
65                  70                  75                  80

Lys Ser Gln Gln Tyr Asp Leu Asn Ala Leu His Lys Thr Thr Lys Ser
                85                  90                  95

Gln Arg His Leu Gly Gly Ser Gln Gln Leu Leu His Asn Lys Gln Glu
            100                 105                 110

Gly Arg Asp His Asp Lys Ser Lys Gly His Phe His Arg Val Val Ile
        115                 120                 125

His His Lys Gly Gly Lys Ala His Arg Gly Thr Gln Asn Pro Ser Gln
    130                 135                 140

Asp Gln Gly Asn Ser Pro Ser Gly Lys Gly Ile Ser Ser Gln Tyr Ser
145                 150                 155                 160

Asn Thr Glu Glu Arg Leu Trp Val His Gly Leu Ser Lys Glu Gln Thr
                165                 170                 175
```

```
Ser Val Ser Gly Ala Gln Lys Gly Arg Lys Gln Gly Gly Ser Gln Ser
            180                 185                 190

Ser Tyr Val Leu Gln Thr Glu Glu Leu Val Ala Asn Lys Gln Gln Arg
            195                 200                 205

Glu Thr Lys Asn Ser His Gln Asn Lys Gly His Tyr Gln Asn Val Val
        210                 215                 220

Glu Val Arg Glu His Ser Ser Lys Val Gln Thr Ser Leu Cys Pro
225                 230                 235                 240

Ala His Gln Asp Lys Leu Gln His Gly Ser Lys Asp Ile Phe Ser Thr
            245                 250                 255

Gln Asp Glu Leu Leu Val Tyr Asn Lys Asn Gln His Gln Thr Lys Asn
        260                 265                 270

Leu Asn Gln Asp Gln Gln His Gly Arg Lys Ala Asn Lys Ile Ser Tyr
        275                 280                 285

Gln Ser Ser Thr Glu Glu Arg Arg Leu His Tyr Gly Glu Asn Gly
    290                 295                 300

Val Gln Lys Asp Val Ser Gln Ser Ser Ile Tyr Ser Gln Thr Glu Glu
305                 310                 315                 320

Lys Ala Gln Gly Lys Ser Gln Lys Gln Ile Thr Ile Pro Ser Gln Glu
            325                 330                 335

Gln Glu His Ser Gln Lys Ala Asn Lys Ile Ser Tyr Gln Ser Ser Ser
        340                 345                 350

Thr Glu Glu Arg Arg Leu His Tyr Gly Glu Asn Gly Val Gln Lys Asp
        355                 360                 365

Val Ser Gln Arg Ser Ile Tyr Ser Gln Thr Glu Lys Leu Val Ala Gly
        370                 375                 380

Lys Ser Gln Ile Gln Ala Pro Asn Pro Lys Gln Glu Pro Trp His Gly
385                 390                 395                 400

Glu Asn Ala Lys Gly Glu Ser Gly Gln Ser Thr Asn Arg Glu Gln Asp
            405                 410                 415

Leu Leu Ser His Glu Gln Lys Gly Arg His Gln His Gly Ser His Gly
            420                 425                 430

Gly Leu Asp Ile Val Ile Ile Glu Gln Glu Asp Asp Ser Asp Arg His
            435                 440                 445

Leu Ala Gln His Leu Asn Asn Asp Arg Asn Pro Leu Phe Thr
    450                 455                 460

<210> SEQ ID NO 2
<211> LENGTH: 402
<212> TYPE: PRT
<213> ORGANISM: Homo sapiens

<400> SEQUENCE: 2

Met Lys Pro Asn Ile Ile Phe Val Leu Ser Leu Leu Ile Leu Glu
 1               5                  10                  15

Lys Gln Ala Ala Val Met Gly Gln Lys Gly Gly Ser Lys Gly Arg Leu
            20                  25                  30

Pro Ser Glu Phe Ser Gln Phe Pro His Gly Gln Lys Gly Gln His Tyr
        35                  40                  45

Ser Gly Gln Lys Gly Lys Gln Gln Thr Glu Ser Lys Gly Ser Phe Ser
    50                  55                  60

Ile Gln Tyr Thr Tyr His Val Asp Ala Asn Asp His Asp Gln Ser Arg
65                  70                  75                  80

Lys Ser Gln Gln Tyr Asp Leu Asn Ala Leu His Lys Thr Thr Lys Ser
                85                  90                  95
```

```
Gln Arg His Leu Gly Gly Ser Gln Gln Leu His Asn Lys Gln Glu
            100                 105                 110

Gly Arg Asp His Asp Lys Ser Lys Gly His Phe His Arg Val Val Ile
        115                 120                 125

His His Lys Gly Gly Lys Ala His Arg Gly Thr Gln Asn Pro Ser Gln
130                 135                 140

Asp Gln Gly Asn Ser Pro Ser Gly Lys Gly Ile Ser Ser Gln Tyr Ser
145                 150                 155                 160

Asn Thr Glu Glu Arg Leu Trp Val His Gly Leu Ser Lys Glu Gln Thr
                165                 170                 175

Ser Val Ser Gly Ala Gln Lys Gly Arg Lys Gln Gly Ser Gln Ser
            180                 185                 190

Ser Tyr Val Leu Gln Thr Glu Glu Leu Val Ala Asn Lys Gln Arg
        195                 200                 205

Glu Thr Lys Asn Ser His Gln Asn Lys Gly His Tyr Gln Asn Val Val
210                 215                 220

Glu Val Arg Glu Glu His Ser Ser Lys Val Gln Thr Ser Leu Cys Pro
225                 230                 235                 240

Ala His Gln Asp Lys Leu Gln His Gly Ser Lys Asp Ile Phe Ser Thr
                245                 250                 255

Gln Asp Glu Leu Leu Val Tyr Asn Lys Asn Gln His Gln Thr Lys Asn
            260                 265                 270

Leu Asn Gln Asp Gln Gln His Gly Arg Lys Ala Asn Lys Ile Ser Tyr
        275                 280                 285

Gln Ser Ser Thr Glu Glu Arg Arg Leu His Tyr Gly Glu Asn Gly
            290                 295                 300

Val Gln Lys Asp Val Ser Gln Arg Ser Ile Tyr Ser Gln Thr Glu Lys
305                 310                 315                 320

Leu Val Ala Gly Lys Ser Gln Ile Gln Ala Pro Asn Pro Lys Gln Glu
                325                 330                 335

Pro Trp His Gly Glu Asn Ala Lys Gly Glu Ser Gly Gln Ser Thr Asn
            340                 345                 350

Arg Glu Gln Asp Leu Leu Ser His Glu Gln Lys Gly Arg His Gln His
        355                 360                 365

Gly Ser His Gly Gly Leu Asp Ile Val Ile Glu Gln Glu Asp Asp
            370                 375                 380

Ser Asp Arg His Leu Ala Gln His Leu Asn Asn Asp Arg Asn Pro Leu
385                 390                 395                 400

Phe Thr

<210> SEQ ID NO 3
<211> LENGTH: 582
<212> TYPE: PRT
<213> ORGANISM: Homo sapiens

<400> SEQUENCE: 3

Met Lys Ser Ile Ile Leu Phe Val Leu Ser Leu Leu Ile Leu Glu
1               5                   10                  15

Lys Gln Ala Ala Val Met Gly Lys Gly Gly Ser Lys Gly Gln Leu
            20                  25                  30

Pro Ser Gly Ser Ser Gln Phe Pro His Gly Gln Lys Gly Gln His Tyr
        35                  40                  45

Phe Gly Gln Lys Asp Gln Gln His Thr Lys Ser Lys Gly Ser Phe Ser
50                  55                  60
```

```
Ile Gln His Thr Tyr His Val Asp Ile Asn Asp His Asp Trp Thr Arg
65                  70                  75                  80

Lys Ser Gln Gln Tyr Asp Leu Asn Ala Leu His Lys Ala Thr Lys Ser
                85                  90                  95

Lys Gln His Leu Gly Gly Ser Gln Gln Leu Leu Asn Tyr Lys Gln Glu
            100                 105                 110

Gly Arg Asp His Asp Lys Ser Lys Gly His Phe His Met Ile Val Ile
        115                 120                 125

His His Lys Gly Gly Gln Ala His His Gly Thr Gln Asn Pro Ser Gln
    130                 135                 140

Asp Gln Gly Asn Ser Pro Ser Gly Lys Gly Leu Ser Ser Gln Cys Ser
145                 150                 155                 160

Asn Thr Glu Lys Arg Leu Trp Val His Gly Leu Ser Lys Glu Gln Ala
                165                 170                 175

Ser Ala Ser Gly Ala Gln Lys Gly Arg Thr Gln Gly Gly Ser Gln Ser
            180                 185                 190

Ser Tyr Val Leu Gln Thr Glu Glu Leu Val Val Asn Lys Gln Gln Arg
        195                 200                 205

Glu Thr Lys Asn Ser His Gln Asn Lys Gly His Tyr Gln Asn Val Val
210                 215                 220

Asp Val Arg Glu Glu His Ser Ser Lys Leu Gln Thr Ser Leu His Pro
225                 230                 235                 240

Ala His Gln Asp Arg Leu Gln His Gly Pro Lys Asp Ile Phe Thr Thr
                245                 250                 255

Gln Asp Glu Leu Leu Val Tyr Asn Lys Asn Gln His Gln Thr Lys Asn
            260                 265                 270

Leu Ser Gln Asp Gln Glu His Gly Arg Lys Ala His Lys Ile Ser Tyr
        275                 280                 285

Pro Ser Ser Arg Thr Glu Glu Arg Gln Leu His His Gly Glu Lys Ser
    290                 295                 300

Val Gln Lys Asp Val Ser Lys Gly Ser Ile Ser Ile Gln Thr Glu Glu
305                 310                 315                 320

Lys Ile His Gly Lys Ser Gln Asn Gln Val Thr Ile His Ser Gln Asp
                325                 330                 335

Gln Glu His Gly His Lys Glu Asn Lys Ile Ser Tyr Gln Ser Ser Ser
            340                 345                 350

Thr Glu Glu Arg His Leu Asn Cys Gly Glu Lys Gly Ile Gln Lys Gly
        355                 360                 365

Val Ser Lys Gly Ser Ile Ser Ile Gln Thr Glu Glu Gln Ile His Gly
    370                 375                 380

Lys Ser Gln Asn Gln Val Arg Ile Pro Ser Gln Ala Gln Glu Tyr Gly
385                 390                 395                 400

His Lys Glu Asn Lys Ile Ser Tyr Gln Ser Ser Thr Glu Glu Arg
                405                 410                 415

Arg Leu Asn Ser Gly Glu Lys Asp Val Lys Gly Val Ser Lys Gly
            420                 425                 430

Ser Ile Ser Ile Gln Thr Glu Glu Lys Ile His Gly Lys Ser Gln Asn
        435                 440                 445

Gln Val Thr Ile Pro Ser Gln Asp Gln Glu His Gly His Lys Glu Asn
    450                 455                 460

Lys Met Ser Tyr Gln Ser Ser Ser Thr Glu Glu Arg Arg Leu Asn Tyr
465                 470                 475                 480
```

```
Gly Gly Lys Ser Thr Gln Lys Asp Val Ser Gln Ser Ile Ser Phe
                485                 490                 495

Gln Ile Glu Lys Leu Val Glu Gly Lys Ser Ile Gln Thr Pro Asn
            500                 505                 510

Pro Asn Gln Asp Gln Trp Ser Gly Gln Asn Ala Lys Gly Lys Ser Gly
            515                 520                 525

Gln Ser Ala Asp Ser Lys Gln Asp Leu Leu Ser His Glu Gln Lys Gly
            530                 535                 540

Arg Tyr Lys Gln Glu Ser Glu Ser His Asn Ile Val Ile Thr Glu
545                 550                 555                 560

His Glu Val Ala Gln Asp Asp His Leu Thr Gln Gln Tyr Asn Glu Asp
                565                 570                 575

Arg Asn Pro Ile Ser Thr
            580

<210> SEQ ID NO 4
<211> LENGTH: 375
<212> TYPE: PRT
<213> ORGANISM: Homo sapiens

<400> SEQUENCE: 4

Met Lys Ser Ser Val Phe Val Leu Ser Leu Leu Ile Leu Glu Arg
 1               5                  10                  15

Gln Ser Ala Val Phe Val Gln Tyr Gly Ala Thr Lys Gly His Phe Gln
                20                  25                  30

Ser Ser Ser Ser Glu Gly Phe Met Leu Gly Gln Lys Gly Arg Leu Ser
            35                  40                  45

Phe Gly Ile Lys Gly Gly Ser Asp Glu Ala Ala Glu Glu Ser Leu Phe
 50                  55                  60

Met Gln Ser Gln Arg Arg Val Tyr Gly Gln Gly Gly Asp Met Thr
65                  70                  75                  80

Gln Thr Arg Val Ser Gln Glu His Thr Ser Val Lys Gly Ala Ala Leu
                85                  90                  95

Cys Arg Asn Gly Gln Val Ser Gln Leu Lys Ser Gln Glu Ser Gln Ile
            100                 105                 110

Lys Ser Tyr Gly Gln Val Lys Ser Ser Gly Gln Leu Lys Ser Gly Gly
        115                 120                 125

Ser Ala Phe Gly Gln Val Lys Ser Ser Val Ser Gln Ile Lys Ser Tyr
    130                 135                 140

Gly Gln Leu Lys Ser Gly Gly Gln Leu Lys Ser Gly Gly Pro Ala Phe
145                 150                 155                 160

Gly Gln Val Lys Ser Gln Glu Ser Gln Ile Lys Ser Tyr Gly Gln Leu
                165                 170                 175

Lys Ser Ser Gly Gln Leu Lys Ser Gly Ser Ala Phe Gly Gln Val
            180                 185                 190

Lys Ser Ser Val Ser Gln Ile Lys Ser Tyr Gly Gln Leu Lys Ser Gly
        195                 200                 205

Gly Ser Gln Val Lys Ser Tyr Gly Gln Thr Lys Ser Tyr Gly Glu Glu
    210                 215                 220

Gly Gln Leu Asn Ser Phe Ser Gln Leu Lys Ser Gln Gly Ala Gln Leu
225                 230                 235                 240

Lys Ser Tyr Gly Gln Gln Lys Ser Gln Gln Ser Ser Phe Ser Gln
                245                 250                 255

Val Lys Ser Gln Ser Ser Gln Leu Lys Ser Tyr Gly Gln Gln Lys Ser
            260                 265                 270
```

```
Leu Lys Gly Phe Ser Gln Gln Thr Gln His Lys Gly Phe Ala Met Asp
            275                 280                 285

Glu Gly Met Ser Gln Val Arg Lys Gln Phe Ser Asp Asp Leu Ser
        290                 295                 300

Val Gln Lys Ser Thr Gln Gln Met Lys Thr Glu Asp Leu Ser
305                 310                 315                 320

Gln Phe Gly Gln Gln Arg Gln Tyr Gly Gln Glu Arg Ser Gln Ser Tyr
                325                 330                 335

Lys Gly Tyr Leu Glu Gln Tyr Arg Lys Val Gln Glu Gln Gln Arg
            340                 345                 350

Lys Asn Phe Asn Pro Gly Asn Tyr Phe Thr Lys Gly Gly Ala Asp Leu
            355                 360                 365

Tyr Gln Ala Gln Leu Lys Gly
            370                 375

<210> SEQ ID NO 5
<211> LENGTH: 414
<212> TYPE: PRT
<213> ORGANISM: Homo sapiens

<400> SEQUENCE: 5

Met Lys Ser Ser Val Phe Ile Leu Ser Leu Phe Leu Leu Glu Arg
  1               5                  10                  15

Gln Ala Ala Val Val Gly Gln Tyr Gly Gly Thr Lys Gly His Phe Gln
                 20                  25                  30

Ser Ser Ser Ser Gly Phe Met Leu Gly Gln Lys Gly His Leu Asn Phe
            35                  40                  45

Gly Leu Lys Gly Gly Ser Glu Glu Ala Ala Glu Glu Ser Ile Phe Met
        50                  55                  60

Gln Ser Gln His Gln Met Phe Gly Gln Asp Gly Gly Asp Met Ala Gln
 65                  70                  75                  80

Thr Ser Val Ser Gln Glu His Thr Gly Val Lys Gly Ala Ala Ile Cys
                 85                  90                  95

Arg Lys Gly Gln Val Ser Gln Leu Lys Ser Gln Glu Ser Gln Ile Lys
            100                 105                 110

Ser Phe Arg Gln Val Lys Ser Ser Gly Gln Leu Lys Ser Gly Gly Ser
            115                 120                 125

Gln Leu Lys Ser Phe Gly Gln Val Lys Ser Ser Glu Ser Gln Leu Lys
        130                 135                 140

Ser Phe Gly Gln Val Lys Ala Ser Gly Ser Gln Leu Lys Ser Phe Gly
145                 150                 155                 160

Gln Val Lys Ala Ser Gly Ser Gln Leu Lys Ser Tyr Gly Gln Met Lys
                165                 170                 175

Ser Ser Gly Ser Gln Val Lys Ser Phe Gly Gln Met Lys Ser Ser Gly
            180                 185                 190

Ser Gln Val Lys Ser Phe Gly Gln Met Lys Ala Ser Glu Ser Gln Ile
        195                 200                 205

Lys Ser Phe Gly Gln Arg Lys Ser Gly Gly Gln Leu Gln Ser Tyr
            210                 215                 220

Gly Gln Met Lys Ser Tyr Gly Thr Lys Ser Leu Glu Ser Gln Ala
225                 230                 235                 240

Lys Ser Phe Gly Gln Val Lys Ser Gln Ser Gly Gln Met Lys Ser Ser
                245                 250                 255

Tyr Gly Gln Arg Lys Ser Tyr Gly Glu Glu Thr Gln Leu Lys Ser Phe
```

```
                260                 265                 270
Asp Gln Asp Ala Gln Leu Lys Ser Tyr Gly Gln Gln Lys Ser Gln Lys
            275                 280                 285

Gln Ser Ser Phe Ser Gln Val Lys Ser Gln Ser Ala Gln Leu Lys Ser
        290                 295                 300

Phe Gly Gln Gln Lys Ser Leu Lys Gly Phe Ser Gln Gln Thr Gln Gln
305                 310                 315                 320

Lys Gly Phe Ala Met Asp Glu Asp Leu Ser Gln Val Arg Lys Gln Phe
                325                 330                 335

Asp Asp Asp Asp Leu Ser Val Gln Gln Lys Ser Thr Gln Gln Met Lys
            340                 345                 350

Thr Glu Glu Asp Leu Ser Gln Phe Gly Gln Gln Arg Gln Phe Gly Gln
        355                 360                 365

Glu Arg Ser Gln Ser Tyr Lys Gly Tyr Leu Ala Gln Tyr Arg Lys Lys
        370                 375                 380

Leu Gln Glu Gln Gln Gln Lys Asn Phe Asn Gln Asp Asn Phe Phe
385                 390                 395                 400

Thr Lys Gly Gly Ala Gly Leu Tyr Gln Ala Gln Leu Lys Gly
                405                 410
```

PROSTATITIS-ASSOCIATED ANTIGENS AND METHODS OF USE THEREOF

CROSS-REFERENCE

This application claims the benefit of U.S. Provisional Patent Application No. 61/168,506, filed Apr. 10, 2009, which application is incorporated herein by reference in its entirety.

STATEMENT REGARDING FEDERALLY SPONSORED RESEARCH

This invention was made with government support under grant numbers R01 CA102303 and U19 AI056388, awarded by the National Institutes of Health. The government has certain rights in the invention.

BACKGROUND

Prostatitis is a highly prevalent disease for men. While acute prostatitis is commonly caused by bacterial infection, most patients with chronic prostatitis/chronic pelvic pain syndrome (CPPS) have no evidence of urinary tract infection. Moreover, a significant proportion of men can have non-infectious chronic prostatitis in the form of asymptomatic inflammatory prostatitis that is diagnosed on prostate biopsy performed to evaluate for prostate cancer. CPPS is in fact the most common non-malignant diagnosis in patients being evaluated for elevated serum levels of prostate specific antigen (PSA), a biomarker used to screen for prostate cancer. The diagnosis of this syndrome currently relies on reported pain in the perineum, rectum, and/or prostate by affected men. CPPS often relapses and remits without clear triggers. Therapy for CPPS is non-specific and usually involves empiric treatment with antibiotics of unclear efficacy. The etiology of CPPS is unknown.

Spontaneous prostatitis has been described in several aged rat strains and even in the aged nonobese diabetic (NOD) mice, but the mechanism by which these strains render the host susceptible to prostatitis is unclear. To date, none of the prostate antigens identified in these mouse models has been shown to be relevant for the human disease.

There is a need in the art for improved methods for diagnosing CPPS.

LITERATURE

U.S. Patent Publication No. 2008/0268463; U.S. Patent Publication No. 2009/0060842.

SUMMARY OF THE INVENTION

The present disclosure provides prostatitis-associated antigens, and compositions comprising the antigens. The present disclosure provides diagnostic methods, generally involving assaying the level of an immune response specific for a prostatitis-associated antigen in an individual. Kits suitable for use in performing such diagnostic assays are also provided. The present disclosure further provides methods of treating prostatitis, methods of treating prostate cancer, and methods of treating benign prostatic hyperplasia.

BRIEF DESCRIPTION OF THE DRAWINGS

FIGS. 9A-E depict amino acid sequences of human semenogelin I isoform a (FIG. 9A), human semenogelin I isoform b (FIG. 9B), human semenogelin II (FIG. 9C), mouse SVS2 (FIG. 9D), and rat SVS2 (FIG. 9E).

DEFINITIONS

Figure 1:
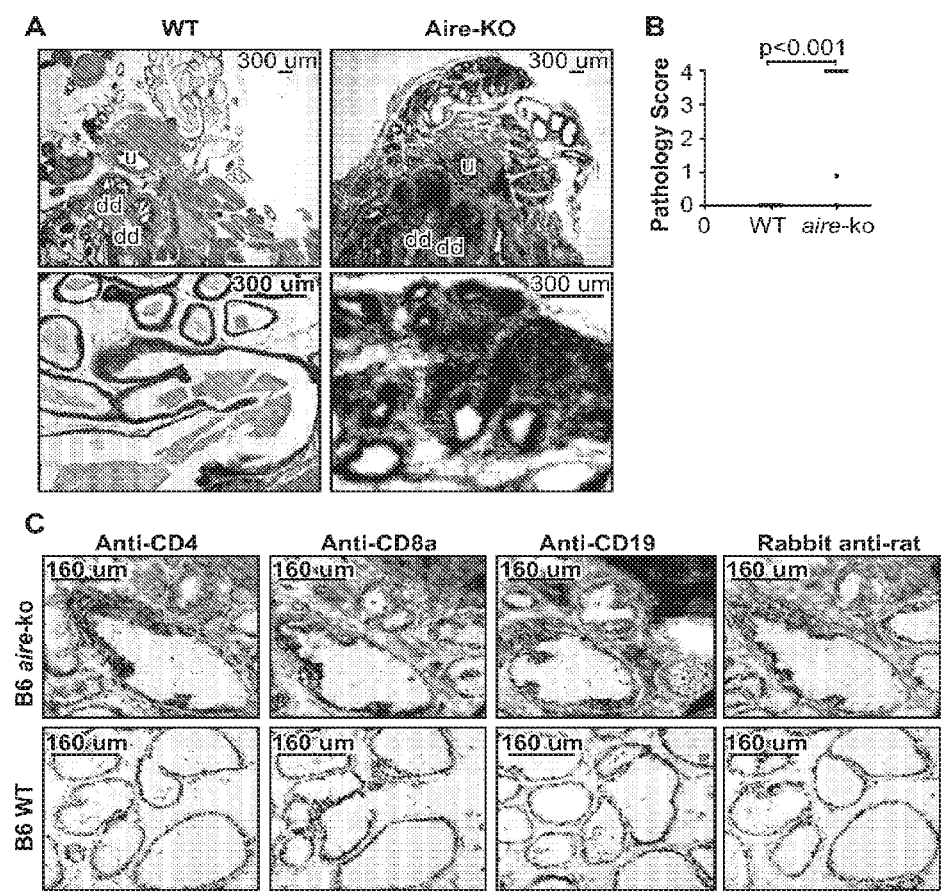
FIGS. 1A-C depict the spontaneous development of autoimmune prostatitis in the Aire-KO mouse.

As used herein, a "biological sample" encompasses a variety of sample types obtained from an individual and can be used in a diagnostic or monitoring assay. The term "biological sample" encompasses semen, blood, and other liquid samples of biological origin, solid tissue samples such as a biopsy specimen or tissue cultures or cells derived therefrom and the progeny thereof. The term "biological sample" also includes samples that have been manipulated in any way after their procurement, such as by treatment with reagents; washed; or enrichment for certain cell populations, such as splenocytes, $CD4^+$ T lymphocytes, $CD8^+$ T lymphocytes, macrophages, tumor cells, peripheral blood mononuclear cells (PBMC), cancer cells, and the like. The term "biological sample" encompasses a clinical sample, and also includes cells in culture, cell supernatants, seminal fluid, semen, tissue samples, organs, bone marrow, blood, plasma, serum, and the like.

The terms "polypeptide," "peptide," and "protein," used interchangeably herein, refer to a polymeric form of amino acids of any length, which can include coded and non-coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; and the like. $NH_2$ refers to the free amino group present at the amino terminus of a polypeptide. COOH refers to the free carboxyl group present at the carboxyl terminus of a polypeptide. In keeping with standard polypeptide nomenclature, *J. Biol. Chem.*, 243 (1969), 3552-59 is used.

As used herein, the terms "label" and "detectable label" refer to a molecule capable of detection, including, but not limited to, radioactive isotopes, fluorescers, chemiluminescers, chromophores, enzymes, enzyme substrates, enzyme cofactors, enzyme inhibitors, dyes, metal ions, metal sols, ligands (e.g., biotin, avidin, streptavidin, haptens, and the like), intercalating dyes, and the like. The term "fluorescer" refers to a substance or a portion thereof which is capable of exhibiting fluorescence in the detectable range.

As used herein the term "isolated" is meant to describe a polynucleotide, a polypeptide, or a cell that is in an environment different from that in which the polynucleotide, the polypeptide, or the cell naturally occurs. An isolated genetically modified host cell may be present in a mixed population of genetically modified host cells. An isolated polypeptide will in some embodiments be synthetic. "Synthetic polypeptides" are assembled from amino acids, and are chemically synthesized in vitro, e.g., cell-free chemical synthesis, using procedures known to those skilled in the art. An isolated polypeptide will in some embodiments be purified.

By "purified" is meant a compound of interest (e.g., a polypeptide) has been separated from components that accompany it in nature. "Purified" can also be used to refer to a compound of interest (e.g., a polypeptide) separated from components that can accompany it during manufacture (e.g., in chemical synthesis). In some embodiments, a compound (e.g., a polypeptide) is substantially pure when it is at least 50% to 60%, by weight, free from organic molecules with which it is naturally associated or with which it is associated during manufacture. In some embodiments, the preparation is at least 75%, at least 90%, at least 95%, at least 98%, or at least 99%, by weight, of the compound of interest. Thus, e.g., a subject polypeptide that is "purified" is present in a composition where the polypeptide is present in an amount of at least 75%, at least 90%, at least 95%, at least 98%, or at least 99%, by weight, of the composition. A substantially pure polypeptide can be obtained, for example, by extraction from a natural source, by recombinant production in a genetically modified host cell, by chemically synthesis, or by a combination of purification and chemical modification. A substantially pure compound can also be obtained by, for example, enriching a sample having a compound that binds an antibody of interest. Purity can be measured by any appropriate method, e.g., chromatography, mass spectroscopy, high performance liquid chromatography analysis, etc.

An "antigen" is defined herein to include any substance that may be specifically bound by an antibody molecule or a T cell receptor. An "immunogen" is an antigen that is capable of initiating lymphocyte activation resulting in an antigen-specific immune response.

By "epitope" is meant a site on an antigen to which specific B cells and/or T cells respond. The term is also used interchangeably with "antigenic determinant" or "antigenic determinant site." B cell epitope sites on proteins, polysaccharides, or other biopolymers may be composed of moieties from different parts of the macromolecule that have been brought together by folding. Epitopes of this kind are referred to as conformational or discontinuous epitopes, since the site is composed of segments of the polymer that are discontinuous in the linear sequence but are continuous in the folded conformation(s). Epitopes that are composed of single segments of biopolymers or other molecules are termed continuous or linear epitopes. T cell epitopes are generally linear peptides. Antibodies that recognize the same epitope can be identified in a simple immunoassay showing the ability of one antibody to block the binding of another antibody to a target antigen.

The term "monoclonal antibody" as used herein refers to an antibody obtained from a population of substantially homogeneous antibodies, i.e., the individual antibodies comprising the population are identical except for possible naturally occurring mutations that may be present in minor amounts.

Monoclonal antibodies included hybrid and recombinant antibodies (e.g. "humanized" antibodies) regardless of species of origin or immunoglobulin class or subclass designation, as well as antibody fragments (e.g., Fab, F(ab')$_2$, and Fv), so long as they are capable of binding specifically to a target antigen as described herein. Cabilly, et al., U.S. Pat. No. 4,816,567; Mage & Lamoyi, in Monoclonal Antibody Production Techniques and Applications, pp. 79-97 (Marcel Dekker, Inc., New York, 1987).

Thus, the modifier "monoclonal" indicates the character of the antibody as being obtained from such a substantially homogeneous population of antibodies, and is not to be construed as requiring production of the antibody by any particular method. For example, the monoclonal antibodies of the invention may be made using the hybridoma method first described by Kohler & Milstein, Nature 256:495 (1975), or may be made by recombinant DNA methods. Cabilly, et al., U.S. Pat. No. 4,816,567.

The terms "subject," "individual," "host," and "patient" are used interchangeably herein to refer to a mammal, including, but not limited to, murines (rats, mice), felines, non-human primates (e.g., simians), humans, canines, ungulates, etc.

The terms "treatment," "treating," "treat," and the like are used herein to generally refer to obtaining a desired pharmacologic and/or physiologic effect. The effect may be prophylactic in terms of completely or partially preventing a disease or symptom thereof and/or may be therapeutic in terms of a partial or complete stabilization or cure for a disease and/or adverse effect attributable to the disease. "Treatment" as used herein covers any treatment of a disease in a mammal, e.g., a human, and includes: (a) preventing the disease or symptom from occurring in a subject which may be predisposed to the disease or symptom but has not yet been diagnosed as having it; (b) inhibiting the disease symptom, i.e., arresting its development; or (c) relieving the disease symptom, i.e., causing regression of the disease or symptom.

As used herein in the context of patient response to treatment with an immunomodulatory treatment regimen, the terms "beneficial response," "beneficial patient response," and "clinically beneficial response," "clinical benefit," and the like, are used interchangeably and include partial response (PR), complete response (CR), and stabilization of disease (SD).

Beneficial response to treatment with an immunomodulatory treatment regimen can be assessed according to whether an individual patient experiences a desirable change in disease status. Examples of desirable change in disease status in prostatitis include a decrease in inflammatory response; decrease in urination frequency; lessening of pain in urination; loss of pelvic, groin or back pain; and a decrease in the level of prostate-specific antigen. Continued increase in the above-mentioned symptoms indicates a lack of beneficial response to treatment.

As used herein, in the context of prostatitis, the term "responder" refers to a patient who has prostatitis, and who exhibits a beneficial clinical response following treatment with an immunomodulatory treatment regimen.

As used herein, in the context of prostatitis, the term "non-responder" refers to a patient who has prostatitis, and who has not shown a beneficial response following treatment with an immunomodulatory treatment regimen.

As used herein, the term "correlates," or "correlates with," and like terms, refers to a statistical association between instances of two events, where events include numbers, data sets, and the like. For example, when the events involve numbers, a positive correlation (also referred to herein as a "direct correlation") means that as one increases, the other increases as well. A negative correlation (also referred to herein as an "inverse correlation") means that as one increases, the other decreases.

The term "substantially similar" as used in the context of nucleic acid or amino acid sequence identity refers to two or more sequences which have at least about 50%, at least about 60%, at least about 70%, at least about 75%, at least about 80%, at least about 85%, at least about 90%, at least about 95%, at least about 98%, at least about 99%, or 100% sequence identity.

As used herein "% sequence identity" is determined using the EMBOSS Pairwise Alignment Algorithms tool available from The European Bioinformatics Institute (EMBL-EBI), which is part of the European Molecular Biology Laboratory. This tool is accessible at the website located by placing "www." in front of "ebi.ac.uk/Tools/emboss/align/". This tool utilizes the Needleman-Wunsch global alignment algorithm (Needleman, S. B. and Wunsch, C. D. (1970) J. Mol. Biol. 48, 443-453; Kruskal, J. B. (1983) An overview of sequence comparison In D. Sankoff and J. B. Kruskal, (ed.), Time warps, string edits and macromolecules: the theory and practice of sequence comparison, pp. 1-44 Addison Wesley. Default settings are utilized which include Gap Open: 10.0 and Gap Extend 0.5. The default matrix "Blosum62" is utilized for amino acid sequences and the default matrix "DNAfull" is utilized for nucleic acid sequences.

As used herein, "autoimmune response" refers to the failure of an organism to recognize its own constituent parts as self, which results in an immune response against its own cells and tissues. In certain cases, autoantibodies are generated as a part of the autoimmune response against autoantigens. In some cases, autoreactive immune cells, e.g., autoreactive T cells, are generated as a part of the autoimmune response against autoantigens.

As used herein, "immunological tolerance" refers to the process by which the immune system does not attack an antigen. In a healthy individual, there is adequate immunological tolerance for all the normal self-antigens such that no immune response is mounted unless there is an invasion of a foreign substance or a diseased growth in the individual.

As used herein, "proteins related to SVS2" refers to proteins that share similarities in gene structure, three-dimensional structural and functional domains with seminal vesicle secretory protein 2 (SVS2) in mice. In certain embodiments, proteins related to SVS2 include mouse SVS2, rat SVS2, human semenogelin I, human semenogelin II, and their isoforms. "SVS2-related proteins" may also belong to a group collectively referred as "rapidly evolving substrates for transglutaminase," as described in Lundwall, A. et al. "A novel gene family encoding proteins with highly differing structure because of a rapidly evolving exon." *FEBS Lett.* 374 (1995): 53-56.

The terms "cancer," "neoplasm," and "tumor" are used interchangeably herein to refer to cells which exhibit relatively autonomous growth, so that they exhibit an aberrant growth phenotype characterized by a significant loss of control of cell proliferation. Cells of interest for treatment in the present application include precancerous, malignant, pre-metastatic, metastatic, and non-metastatic cells, as well as carcinoma in situ.

"Cancerous phenotype" generally refers to any of a variety of biological phenomena that are characteristic of a cancerous cell, which phenomena can vary with the type of cancer. The cancerous phenotype is generally identified by abnormalities in, for example, cell growth or proliferation (e.g., uncontrolled growth or proliferation), regulation of the cell cycle, cell mobility, cell-cell interaction, or metastasis, etc.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "an antibody" includes a plurality of such antibodies and reference to "the prostatitis-associated antigen" includes reference to one or more prostatitis-associated antigens and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides prostatitis-associated antigens (PAA), and compositions comprising the antigens. The present disclosure provides diagnostic methods, generally involving assaying the level of an immune response specific for a PAA in an individual. Kits suitable for use in performing such diagnostic assays are also provided. The present disclosure further provides methods of treating prostatitis.

The present disclosure relates to the observation that male individuals affected by chronic prostatitis or chronic pelvic pain syndrome (CPPS) mount an immune response to semenogelin (SG), a protein related to seminal vesicle secretory protein 2 in mice (SVS2). SG and SVS2 share similarities in gene structure, three-dimensional structural and functional domains with other proteins collectively referred to as "rapidly evolving substrates for transglutaminase," as described in Lundwall, A. et al. (1995) *FEBS Lett.* 374:53-56. Identification of these antigens as targets of an autoimmune response allows the development of a diagnostic method for determining the etiology of CPPS or asymptomatic inflammatory prostatitis. Identification of these proteins as immunogenic antigens also provides for the development of immune response modulators, where administration of such a composition to an individual who has prostatitis reduces the symptoms associated with prostatitis. Furthermore, identification of these target antigens allows generation of assays to correctly distinguish prostatitis over other prostate disorders, such as prostate cancer. In certain embodiments, the diagnosis developed based on prostatitis-associated antigen can lessen the need for invasive biopsy.

Prostatitis-Associated Antigens

The present disclosure provides prostatitis-associated antigens (PAA), and compositions comprising the antigens. PAA are useful in various applications, including diagnostic assays and treatment methods.

Target antigens that are the target of an autoimmune response generated in an individual who has prostatitis, e.g. chronic prostatitis, are also referred herein as "self-antigens," "prostatitis-associated antigens," or "prostatitis-associated target antigens." An individual that has lost immunologic tolerance for SG, SVS2, or related proteins may develop autoantibodies or "prostatitis-associated autoantibodies" in response to such self-antigens.

In certain embodiments, PAA are useful in diagnostic assays, as described in more detail below, to detect an antibody response in a prostatitis patient who has not yet undergone treatment for the prostatitis, e.g., to correctly diagnose prostatitis from other prostate disorders, e.g. prostate cancer, and to determine likelihood of beneficial clinical response to treatment with an immunomodulatory treatment regimen. PAA are also useful, as described below, to detect an antibody response in a prostatitis patient for prognosis during treatment, e.g., to determine likelihood of beneficial clinical response to treatment with an immunomodulatory treatment regimen. PAA are also useful in immunogenic compositions, to induce an immune response to the target antigen, e.g., in an animal to model human prostatitis. In other embodiments, PAA are also useful for generating therapeutic antibodies, which antibodies are useful for treating prostatitis.

PAA are targets of an autoimmune response generated in an individual who has chronic prostatitis or CPPS and who may exhibit a clinically beneficial response to treatment with an immunomodulatory treatment regimen. As used herein "PAA" includes, but is not limited to, human semenogelin (SG) I isoform a; human semenogelin I isoform b; human semenogelin II; mouse SVS2; active fragments of a PAA; a polypeptide comprising an amino acid sequence that is substantially similar to the amino acid sequence of a human SG or a rodent SVS2 polypeptide; a fusion polypeptide comprising a PAA and a heterologous fusion partner; a synthetic PAA; and the like. Amino acid sequences of human SG are available at, e.g., GenBank Accession Numbers: NP_002998 (Semenogelin I), NP_002999 (Semenogelin II); and UniProtKB/Swiss-Prot Accession Numbers: P04279 (SEMG1_Human), and Q02328 (SEMG2_Human).

A polypeptide comprising an amino acid sequence that is substantially similar to the amino acid sequence of a human SG or a rodent SVS2 polypeptide includes a polypeptide comprising an amino acid sequence having at least about 70%, at least about 75%, at least about 80%, at least about 85%, at least about 90%, at least about 95%, at least about 98%, or at least about 99%, amino acid sequence identity to a contiguous stretch of from about 25 amino acids (aa) to about 50 aa, from about 50 aa to about 75 aa, from about 75 aa to about 100 aa, from about 100 aa to about 150 aa, from about 150 aa to about 200 aa, from about 200 aa to about 250 aa, from about 250 aa to about 300 aa, from about 300 aa to about 350 aa, from about 350 aa to about 400 aa, from about 400 aa to about 450 aa, from about 450 aa to about 500 aa, from about 500 aa to about 550 aa, or from about 550 aa to about 580 aa, of a human SG (e.g., a human SG comprising SEQ ID NO:1; SEQ ID NO:2; or SEQ ID NO:3) or a rodent SVS2 polypeptide (e.g., a rodent SVS2 comprising SEQ ID NO:4; SEQ ID NO:5).

The present disclosure provides an isolated PAA, antigenic fragments of a PAA, and variants of a PAA. In some embodiments, a subject PAA is isolated from a natural source, e.g., is in an environment other than its naturally-occurring environment. In other embodiments, a subject PAA is recombinantly made, e.g., in a genetically modified host cell (e.g., bacteria; yeast; *Picchia*; insect cells; and the like), where the genetically modified host cell is genetically modified with a nucleic acid comprising a nucleotide sequence encoding the PAA. In certain cases, the PAA is synthetic, e.g., a subject synthetic PAA is synthesized chemically in a laboratory (e.g., by cell-free chemical synthesis). The PAA can be a full-length or one or more fragments of SG, SVS2, or proteins functionally and structurally similar to SVS2.

In some embodiments, a subject PAA comprises an amino acid sequence having at least about 70%, at least about 75%, at least about 80%, at least about 85%, at least about 90%, at least about 95%, at least about 98%, or at least about 99%, amino acid sequence identity to a contiguous stretch of from about 25 amino acids (aa) to about 50 aa, from about 50 aa to about 75 aa, from about 75 aa to about 100 aa, from about 100 aa to about 150 aa, from about 150 aa to about 200 aa, from about 200 aa to about 250 aa, from about 250 aa to about 300 aa, from about 300 aa to about 350 aa, from about 350 aa to about 400 aa, from about 400 aa to about 450 aa, or from about 450 to about 462 aa, of the amino acid sequence depicted in FIG. 9A (SEQ ID NO:1).

In some embodiments, a subject PAA comprises an amino acid sequence having at least about 70%, at least about 75%, at least about 80%, at least about 85%, at least about 90%, at least about 95%, at least about 98%, or at least about 99%, amino acid sequence identity to a contiguous stretch of from about 25 amino acids (aa) to about 50 aa, from about 50 aa to about 75 aa, from about 75 aa to about 100 aa, from about 100 aa to about 150 aa, from about 150 aa to about 200 aa, from about 200 aa to about 250 aa, from about 250 aa to about 300 aa, from about 300 aa to about 350 aa, or from about 350 aa to about 402 aa, of the amino acid sequence depicted in FIG. 9B (SEQ ID NO:2).

In some embodiments, a subject PAA comprises an amino acid sequence having at least about 70%, at least about 75%, at least about 80%, at least about 85%, at least about 90%, at least about 95%, at least about 98%, or at least about 99%, amino acid sequence identity to a contiguous stretch of from about 25 amino acids (aa) to about 50 aa, from about 50 aa to about 75 aa, from about 75 aa to about 100 aa, from about 100 aa to about 150 aa, from about 150 aa to about 200 aa, from about 200 aa to about 250 aa, from about 250 aa to about 300 aa, from about 300 aa to about 350 aa, from about 350 aa to about 400 aa, from about 400 aa to about 450 aa, from about 450 aa to about 500 aa, from about 500 aa to about 550 aa, or from about 550 aa to about 582 aa, of the amino acid sequence depicted in FIG. 9C (SEQ ID NO:3).

In some embodiments, a subject PAA comprises an amino acid sequence having at least about 70%, at least about 75%, at least about 80%, at least about 85%, at least about 90%, at least about 95%, at least about 98%, or at least about 99%, amino acid sequence identity to a contiguous stretch of from about 25 amino acids (aa) to about 50 aa, from about 50 aa to about 75 aa, from about 75 aa to about 100 aa, from about 100 aa to about 150 aa, from about 150 aa to about 200 aa, from about 200 aa to about 250 aa, from about 250 aa to about 300 aa, from about 300 aa to about 350 aa, or from about 350 aa to about 375 aa, of the amino acid sequence depicted in FIG. 9D (SEQ ID NO:3).

In some embodiments, a subject PAA comprises an amino acid sequence having at least about 70%, at least about 75%, at least about 80%, at least about 85%, at least about 90%, at least about 95%, at least about 98%, or at least about 99%, amino acid sequence identity to a contiguous stretch of from about 25 amino acids (aa) to about 50 aa, from about 50 aa to about 75 aa, from about 75 aa to about 100 aa, from about 100 aa to about 150 aa, from about 150 aa to about 200 aa, from about 200 aa to about 250 aa, from about 250 aa to about 300 aa, from about 300 aa to about 350 aa, from about 350 aa to about 400 aa, or from about 400 aa to about 414 aa, of the amino acid sequence depicted in FIG. 9E (SEQ ID NO:5).

In some embodiments, a subject PAA has a length of from about 15 aa to about 25 aa, from about 25 aa to about 50 aa, from about 50 aa to about 100 aa, from about 100 aa to about 150 aa, from about 150 aa to about 200 aa, from about 200 aa to about 250 aa, from about 250 aa to about 300 aa, from about 300 aa to about 350 aa, from about 350 aa to about 400 aa, from about 400 aa to about 450 aa, from about 450 aa to about 500 aa, from about 500 aa to about 550 aa, or from about 550 aa to about 580 aa. Where a subject PAA is a fusion protein comprising a PAA and a heterologous fusion partner polypeptide, a subject PAA fusion protein can have a total length that is equal to the sum of the PAA and the heterologous fusion partner polypeptide.

In some embodiments, a subject PAA comprises a detectable label, e.g., a radioisotope, an enzyme which generates a detectable product, a fluorescent protein, a chromogenic protein, and the like. A subject PAA can be conjugated to other moieties, such as members of specific binding pairs, e.g., biotin (member of biotin-avidin specific binding pair), an antibody, a lectin, and the like. A subject PAA can also be bound to (e.g., immobilized onto) a solid support, including, but not limited to, polystyrene plates or beads, magnetic beads, test strips, membranes, and the like.

In some embodiments, a subject PAA is detectably labeled, either directly or indirectly. Direct labels include radioisotopes (e.g., $^{125}$I; $^{35}$S, and the like); enzymes whose products generate a signal (e.g., luciferase, β-galactosidase, horse radish peroxidase, alkaline phosphatase, and the like); fluorescent labels (e.g., fluorescein isothiocyanate, rhodamine, phycoerythrin, and the like); fluorescence emitting metals, e.g., $^{152}$Eu, or others of the lanthanide series, attached to the antibody through metal chelating groups such as EDTA; chemiluminescent compounds, e.g., luminol, isoluminol, acridinium salts, and the like; bioluminescent compounds, e.g., luciferin; fluorescent proteins; and the like. Indirect labels include second antibodies specific for a subject antibody, wherein the second antibody is labeled as described above; and members of specific binding pairs, e.g., biotin-avidin, and the like.

In some embodiments, a subject PAA is a fusion protein comprising a PAA and a fusion partner polypeptide such as a fluorescent or chromogenic polypeptide, or an enzyme that generates a product that produces a detectable signal. Suitable enzymes include, but are not limited to, β-galactosidase, luciferase, horse radish peroxidase, alkaline phosphatase, etc. Suitable fluorescent proteins include, but are not limited to, a green fluorescent protein (GFP), including, but not limited to, a GFP derived from *Aequoria victoria* or a derivative thereof, a number of which are commercially available; a GFP from a species such as *Renilla reniformis, Renilla mulleri*, or *Ptilosarcus guernyi*, as described in, e.g., WO 99/49019 and Peelle et al. (2001) *J. Protein Chem.* 20:507-519; a yellow fluorescent protein; a red fluorescent protein; any of a variety of fluorescent and colored proteins from *Anthozoan* species, as described in, e.g., Matz et al. (1999) *Nature Biotechnol.* 17:969-973, U.S. Patent Publication No. 2002/0197676, or U.S. Patent Publication No. 2005/0032085; and the like.

Multimerized PAA

In some embodiments, a subject PAA is multimerized, e.g., two or more PAA polypeptides are linked, e.g., in tandem, or as cross-linked monomeric units. Multimers include dimers, trimers, tetramers, pentamers, etc. Monomeric PAA polypeptides are linked to one another directly or via a linker.

Thus, in some embodiments, a subject PAA polypeptide has the formula $(X_1—(Y)_{0-40}—X_2—(Y)_{0-40})_n$, where $X_1$ and $X_2$ are PAA polypeptides, Y is a linker, and n is an integer from 1 to about 10 (e.g., n=1, 2, 3, 4, 5, 6, 7, 8, 9, or 10). Where a linker is used, Y is one or more amino acids, or other linking groups. $X_1$ and $X_2$ can be the same or different, e.g., can have the same amino acid sequence, or can differ from one another in amino acid sequence. Thus, e.g., a subject PAA polypeptide can have the formula $X_1—(Y)_{0-40}—X_2$, e.g., where the PAA polypeptide is a dimer.

In some embodiments, a subject multimerized PAA is a homodimer, where two monomeric PAA subunits are cross-linked, e.g., via internal amino acid residues such as cysteine residues. In other embodiments, a subject multimerized PAA is a homotrimer, where three monomeric PAA subunits are cross-linked, e.g., via internal amino acid residues such as cysteine residues. In other embodiments, a subject multimerized PAA is a homotetramer, where four monomeric PAA subunits are cross-linked, e.g., via internal amino acid residues such as cysteine residues.

Linkages for homo- or hetero-polymers or for coupling to carriers can be provided in a variety of ways. For example, cysteine residues can be added at both the amino- and carboxyl-termini, where the peptides are covalently bonded via controlled oxidation of the cysteine residues. Also useful are a large number of heterobifunctional agents which generate a disulfide link at one functional group end and a peptide link at the other, including N-succidimidyl-3-(2-pyridyldithio)propionate (SPDP). This reagent creates a disulfide linkage between itself and a cysteine residue in one protein and an amide linkage through the amino on a lysine or other free amino group in the other. A variety of such disulfide/amide forming agents is known. See, for example, Immun. Rev. 62:185 (1982). Other bifunctional coupling agents form a thioether rather than a disulfide linkage. Many of these thioether forming agents are commercially available and include reactive esters of 6-maleimidocaproic acid, 2 bromoacetic acid, 2-iodoacetic acid, 4-(N-maleimido-methyl)cyclohexane-1-carboxylic acid and the like. The carboxyl groups can be activated by combining them with succinimide or 1-hydroxy-2-nitro-4-sulfonic acid, sodium salt. An exemplary coupling agent is succinimidyl 4-(N-maleimidomethyl)cyclohexane-1-carboxylate (SMCC). Of course, it will be understood that linkage should not substantially interfere with either of the linked groups to function for its intended use.

Carriers

In some embodiments, a subject PAA polypeptide is linked to a carrier. The term "linked," as used herein interchangeably with the term "coupled," refers to proximately associated, e.g., the PAA polypeptide and the carrier are in close spatial proximity. In some embodiments, the linkage is a covalent linkage. In other embodiments, the linkage is a non-covalent linkage. In some embodiments, the PAA polypeptide is linked directly to the carrier. In other embodiments, the PAA polypeptide is linked indirectly, e.g., via a linker molecule.

Examples of suitable carriers include large, slowly metabolized macromolecules such as: proteins; polysaccharides, such as sepharose, agarose, cellulose, cellulose beads and the like; polymeric amino acids such as polyglutamic acid, polylysine, and the like; amino acid copolymers; inactivated virus particles; inactivated bacterial toxins such as toxoid from diphtheria, tetanus, cholera, leukotoxin molecules; liposomes; inactivated bacteria; dendritic cells; and the like. Carriers are described in further detail below.

Suitable carriers are well known in the art, and include, e.g., thyroglobulin, albumins such as human serum albumin, tetanus toxoid; Diphtheria toxoid; polyamino acids such as poly(D-lysine:D-glutamic acid); VP6 polypeptides of rotaviruses; influenza virus hemagglutinin, influenza virus nucleoprotein; hepatitis B virus core protein, hepatitis B virus surface antigen; purified protein derivative (PPD) of tuberculin from *Mycobacterium tuberculosis*; inactivated *Pseudomonas aeruginosa* exotoxin A (toxin A); Keyhole Limpet Hemocyanin (KLH); filamentous hemagglutinin (FHA) of *Bordetella pertussis*; T helper cell (Th) epitopes of tetanus toxoid (TT) and Bacillus Calmette-Guerin (BCG) cell wall; recombinant 10 kDa, 19 kDa and 30-32 kDa proteins from *M. leprae* or from *M. tuberculosis*, or any combination of these proteins; and the like. See, e.g., U.S. Pat. No. 6,447,778 for a discussion of carriers, and for methods of conjugating peptides to carriers.

*Pseudomonas aeruginosa* exotoxin A (toxin A) has been used effectively as a carrier in conjugate vaccines. *Pseudomonas aeruginosa* exotoxin A may be purified from the supernatant of fermentor-grown cultures of *Pseudomonas aeruginosa* PA 103. Toxin A has been classified as a superantigen based upon results in animals. Toxin A can be completely and irreversibly detoxified by covalent coupling to adipic acid dihydrazide (ADH), a 4 carbon spacer molecule. This step destroys the ADPR-transferase activity of the toxin molecule, hence rendering it nontoxic. The non-reacted hydrazide group can be used to covalently couple a polypeptide to toxin A. Toxin A may also be coupled to a polypeptide using a carbodiimide reagent.

PPD-peptide conjugates are conveniently prepared with glutaraldehyde as coupling agent. See, e.g., Rubinstein et al. (1995) *AIDS* 9:243-51.

The methods by which a subject polypeptide is conjugated with a carrier include disulfide linkages through a C terminal peptide cysteine linkage, coupling with glutaraldehyde solution for two hours, coupling with tyrosine, or coupling with water soluble carbodiimide.

In some embodiments, a subject PAA polypeptide is lipidated. Lipidation increases a cytotoxic T cell (CTL) response to the peptide that is linked to the lipid. The lipid residue, such as palmitic acid or the like, is attached to the amino terminus of the peptide. The lipid can be attached directly to the peptide, or, indirectly via a linkage, such as a Ser-Ser, Gly, Gly-Gly, Ser linkage or the like. As another example, *E. coli* lipoprotein, such as tripalmitoyl-S-glycerylcysteinyl-serylserine ($P_3$ CSS), can be used to prime specific CTL when covalently attached to the peptide. See, Deres et al., *Nature* 342:561-564 (1989). A subject PAA polypeptide can be conjugated with uncharged fatty acid residues of different chain lengths and degrees of unsaturation, ranging from acetic to stearic acid as well as to negatively charged succinyl residues via the appropriate carboxylic acid anhydrides. See, e.g., U.S. Pat. No. 6,419,931.

A subject PAA polypeptide may be conjugated directly or indirectly, e.g., via a linker molecule, to a carrier. A wide variety of linker molecules are known in the art and can be used in the conjugates. The linkage from the peptide to the carrier may be through a peptide reactive side chain, or the N- or C-terminus of the peptide. A linker may be an organic, inorganic, or semi-organic molecule, and may be a polymer of an organic molecule, an inorganic molecule, or a co-polymer comprising both inorganic and organic molecules.

If present, the linker molecules are generally of sufficient length to permit the PAA polypeptide and a linked carrier to allow some flexible movement between the PAA polypeptide and the carrier. The linker molecules are generally about 6-50 atoms long. The linker molecules may also be, for example, aryl acetylene, ethylene glycol oligomers containing 2-10 monomer units, diamines, diacids, amino acids, or combinations thereof. Other linker molecules which can bind to polypeptides may be used in light of this disclosure.

Compositions

The present disclosure provides compositions comprising a subject PAA, which in some embodiments are immunogenic compositions. Compositions comprising a subject PAA may include a buffer, which is selected according to the desired use of the PAA, and may also include other substances appropriate to the intended use. Those skilled in the art can readily select an appropriate buffer, a wide variety of which are known in the art, suitable for an intended use. In some instances, the composition can comprise a pharmaceutically acceptable excipient, a variety of which are known in the art and need not be discussed in detail herein. Pharmaceutically acceptable excipients have been amply described in a variety of publications, including, for example, "Remington: The Science and Practice of Pharmacy", $19^{th}$ Ed. (1995), or latest edition, Mack Publishing Co; A. Gennaro (2000) "Remington: The Science and Practice of Pharmacy", 20th edition, Lippincott, Williams, & Wilkins; Pharmaceutical Dosage Forms and Drug Delivery Systems (1999) H. C. Ansel et al., eds $7^{th}$ ed., Lippincott, Williams, & Wilkins; and Handbook of Pharmaceutical Excipients (2000) A. H. Kibbe et al., eds., $3^{rd}$ ed. Amer. Pharmaceutical Assoc.

A subject PAA composition can comprise, in addition to a subject PAA, one or more of: a salt, e.g., NaCl, MgCl, KCl, $MgSO_4$, etc.; a buffering agent, e.g., a Tris buffer, N-(2-Hydroxyethyl)piperazine-N'-(2-ethanesulfonic acid) (HEPES), 2-(N-Morpholino)ethanesulfonic acid (MES), 2-(N-Morpholino)ethanesulfonic acid sodium salt (MES), 3-(N-Morpholino)propanesulfonic acid (MOPS), N-tris[Hydroxymethyl]methyl-3-aminopropanesulfonic acid (TAPS), etc.; a solubilizing agent; a detergent, e.g., a non-ionic detergent such as Tween-20, etc.; a protease inhibitor; glycerol; and the like.

Pharmaceutical compositions can be prepared in various forms, such as granules, tablets, pills, suppositories, capsules, suspensions, sprays, suppositories, transdermal applications (e.g., patches, etc.), salves, lotions and the like. Pharmaceutical grade organic or inorganic carriers and/or diluents suitable for oral and topical use can be used to make up compositions containing the therapeutically active compounds. Diluents known to the art include aqueous media, vegetable and animal oils and fats. Stabilizing agents, wetting and emulsifying agents, salts for varying the osmotic pressure or buffers for securing an adequate pH value, and skin penetration enhancers can be used as auxiliary agents.

Immunogenic Compositions

The present disclosure provides an immunogenic composition comprising a subject PAA. A subject immunogenic composition is useful for inducing in an individual an immune response to a PAA.

In some embodiments, a subject immunogenic composition comprises a PAA and an adjuvant. Suitable adjuvants include those suitable for use in humans. Examples of known suitable adjuvants that can be used in humans include, but are not necessarily limited to, alum, aluminum phosphate, aluminum hydroxide, MF59 (4.3% w/v squalene, 0.5% w/v polysorbate 80 (Tween 80), 0.5% w/v sorbitan trioleate (Span 85)), a CpG-containing nucleic acid (where the cytosine is unmethylated), QS21 (saponin adjuvant), MPL (Monophosphoryl Lipid A), 3DMPL (3-O-deacylated MPL), extracts from Aquilla, ISCOMS (see, e.g., Sjölander et al. (1998) *J. Leukocyte Biol.* 64:713), LT/CT mutants, poly(D,L-lactide-co-glycolide) (PLG) microparticles, Quil A, interleukins, and the like. For veterinary applications including but not limited to animal experimentation, one can use Freund's, N-acetyl-muramyl-L-threonyl-D-isoglutamine (thr-MDP), N-acetyl-nor-muramyl-L-alanyl-D-isoglutamine (CGP 11637, referred to as nor-MDP), N-acetylmuramyl-L-alanyl-D-isoglutaminyl-L-alanine-2-(1'-2'-dipalmitoyl-sn-glycero-3-hydroxyphosphoryloxy)-ethylamine (CGP 19835A, referred to as MTP-PE), and RIBI, which contains three components extracted from bacteria, monophosphoryl lipid A, trehalose dimycolate and cell wall skeleton (MPL+TDM+CWS) in a 2% squalene/Tween 80 emulsion.

Further exemplary adjuvants to enhance effectiveness of the composition include, but are not limited to: (1) oil-in-water emulsion formulations (with or without other specific immunostimulating agents such as muramyl peptides (see below) or bacterial cell wall components), such as for example (a) MF59™ (WO90/14837; Chapter 10 in *Vaccine design: the subunit and adjuvant approach*, eds. Powell & Newman, Plenum Press 1995), containing 5% Squalene, 0.5% Tween 80 (polyoxyethylene sorbitan mono-oleate), and 0.5% Span 85 (sorbitan trioleate) (optionally containing muramyl tri-peptide covalently linked to dipalmitoyl phosphatidylethanolamine (MTP-PE)) formulated into submicron particles using a microfluidizer, (b) SAF, containing 10% Squalane, 0.4% Tween 80, 5% pluronic-blocked polymer L121, and thr-MDP either microfluidized into a submicron emulsion or vortexed to generate a larger particle size emulsion, and (c) RIBI™ adjuvant system (RAS), (Ribi Immunochem, Hamilton, Mont.) containing 2% Squalene, 0.2% Tween 80, and one or more bacterial cell wall components such as monophosphorylipid A (MPL), trehalose dimycolate (TDM), and cell wall skeleton (CWS), e.g., MPL+CWS (DETOX™); (2) saponin adjuvants, such as QS21 or STIMULON™ (Cambridge Bioscience, Worcester, Mass.) may be used or particles generated therefrom such as ISCOMs (immunostimulating complexes), which ISCOMS may be devoid of additional detergent e.g. WO 00/07621; (3) Complete Freund's Adjuvant (CFA) and Incomplete Freund's Adjuvant (IFA); (4) cytokines, such as interleukins (e.g. IL-1, IL-2, IL-4, IL-5, IL-6, IL-7, IL-12 (WO99/44636), etc.), interferons (e.g. gamma interferon), macrophage colony stimulating factor (M-CSF), tumor necrosis factor (TNF), other TNF superfamily molecules (e.g., CH40L, OX40L, and the like), etc.; (5) monophosphoryl lipid A (MPL) or 3-O-deacylated MPL (3dMPL) e.g. GB-2220221, EP-A-0689454, optionally in the substantial absence of alum when used with pneumococcal saccharides e.g. WO00/56358; (6) combinations of 3dMPL with, for example, QS21 and/or oil-in-water emulsions e.g. EP-A-0835318, EP-A-0735898, EP-A-0761231; (7) oligonucleotides comprising CpG motifs (Krieg *Vaccine* 2000, 19, 618-622; Krieg *Curr Opin Mol Ther* 2001 3:15-24; Roman et al., *Nat. Med.*, 1997, 3, 849-854; Weiner et al., *PNAS USA*, 1997, 94, 10833-10837; Davis et al, *J. Immunol*, 1998, 160, 870-876; Chu et al., *J. Exp. Med*, 1997, 186, 1623-1631; Lipford et al, *Eur. J. Immunol.*, 1997, 27, 2340-2344; Moldoveanu et al., *Vaccine*, 1988, 16, 1216-1224, Krieg et al., *Nature*, 1995, 374, 546-549; Klinman et al., *PNAS USA*, 1996, 93, 2879-2883; Ballas et al, *J. Immunol*, 1996, 157, 1840-1845; Cowdery et al, *J. Immunol*, 1996, 156, 4570-4575; Halpern et al, *Cell Immunol*, 1996, 167, 72-78; Yamamoto et al, *Jpn. J. Cancer Res.*, 1988, 79, 866-873; Stacey et al, *J. Immunol.*, 1996, 157, 2116-2122; Messina et al, *J. Immunol*, 1991, 147, 1759-1764; Yi et al, *J. Immunol*, 1996, 157, 4918-4925; Yi et al, *J. Immunol*, 1996, 157, 5394-5402; Yi et al, *J. Immunol*, 1998, 160, 4755-4761; and Yi et al, *J. Immunol*, 1998, 160, 5898-5906; International patent applications WO96/02555, WO98/16247, WO98/18810, WO98/40100, WO98/55495, WO98/37919 and WO98/52581) e.g., containing at least one CG dinucleotide, where the cytosine is unmethylated; (8) a polyoxyethylene ether or a polyoxyethylene ester e.g. WO99/52549; (9) a polyoxyethylene sorbitan ester surfactant in combination with an octoxynol (WO01/21207) or a polyoxyethylene alkyl ether or ester surfactant in combination with at least one additional non-ionic surfactant such as an octoxynol (WO01/21152); (10) a saponin and an immunostimulatory oligonucleotide (e.g. a CpG oligonucleotide) (WO00/62800); (11) an immunostimulant and a particle of metal salt e.g. WO00/23105; (12) a saponin and an oil-in-water emulsion e.g. WO99/11241; (13) a saponin (e.g. QS21)+3dMPL+IM2 (optionally+a sterol) e.g. WO98/57659; (14) other substances that act as immunostimulating agents to enhance the efficacy of the composition. Muramyl peptides include N-acetyl-muramyl-L-threonyl-D-isoglutamine (thr-MDP), N-25 acetyl-normuramyl-L-alanyl-D-isoglutamine (nor-MDP), N-acetylmuramyl-L-alanyl-D-isoglutaminyl-L-alanine-2-(1'-2'-dipalmitoyl-sn-glycero-3-hydroxyphosphoryloxy)-ethylamine MTP-PE), etc.

A subject immunogenic composition can include a conventional pharmaceutically acceptable excipient, such as pharmaceutical grades of mannitol, lactose, starch, magnesium stearate, sodium saccharin, talcum, cellulose, glucose, sucrose, magnesium, carbonate, and the like. A subject immunogenic composition can include one or more pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of antigen (e.g., a PAA) in these formulations can vary widely, and can be selected based on various factors such as fluid volumes, viscosities, body weight and the like in accordance with the particular mode of administration selected and the patient's needs. The resulting compositions may be in the form of a solution, suspension, tablet, pill, capsule, powder, gel, cream, lotion, ointment, aerosol or the like.

The PAA concentration of a subject immunogenic composition in the pharmaceutical formulations can vary widely, e.g., less than about 0.1%, from about 0.1% to about 2%, from about 2% to 20%, or from about 20% to about 50%, or more, by weight, and will be selected on the basis of various factors such as fluid volumes, viscosities, etc., in accordance with the particular mode of administration selected.

Diagnostic Methods

The present disclosure provides methods of diagnosing autoimmune-mediated prostatitis (e.g., non-bacterial prostatitis); methods for monitoring patient response to treatment for chronic (non-bacterial) prostatitis; methods of distinguishing prostate cancer from prostatitis; and methods of evaluating the cause of male sterility. The methods generally involve detecting a level of antibody to a PAA in a male individual.

Diagnosing Non-Bacterial Prostatitis or CPPS

In certain embodiments, the present disclosure provides methods of determining whether a patient has chronic prostatitis or CPPS caused by an autoimmune response against PAA. A subject diagnostic method generally involves detecting the level of PAA-specific antibody and/or PAA-specific T cells in a biological sample obtained from a male individual.

In some cases, a subject diagnostic method can entail determining a baseline value of an immune response in a normal control, and comparing this with a value for the test immune response. A significantly high (i.e., greater than the typical margin of experimental error in repeat measurements of the same sample, expressed as one standard deviation from the mean of such measurements) level of the immune response relative to a normal control signals the presence of an autoimmune response against the PAA in the sample. If the value for immune response is not significantly different, this signals the lack of an autoimmune response against the prostatitis-associated antigen. In other methods, a normal control value (i.e., a mean and standard deviation) of immune response is determined for a control population. Typically the individuals in the control population are free of chronic (non-bacterial) prostatitis. Measured values of immune response in a patient may be compared with the normal control value.

Thus, for example, a test level of an indicator of an immune response to a PAA (e.g., a level of PAA-specific antibody; a level of PAA-specific T cells) in a test individual is compared to a reference level of the indicator. The term "a reference level" refers to a level of PAA-specific antibody or a level of PAA-specific T cell that is present in a subject(s) that is/are asymptomatic for CP/CPPS. The "reference level" can be an average level of an indicator of an immune response to PAA (e.g. an average level of PAA-specific antibody or an average level of PAA-specific T cell) obtained from data from multiple subjects that are asymptomatic for CP/CPPS. Alternatively, a test sample can be compared directly to the level present in a control sample, e.g. when testing pre-treatment versus post-treatment (see below).

For example, a normal control level (or reference control level) of an immune response can be readily determined by determining the level of antibodies against PAA in a statistically significant number of individuals who do not have prostatitis or who do not have an autoimmune response against PAA. In certain cases, a positive control level is a range of level of autoantibody generated in an autoimmune response detected in a statistically significant number of individuals who have chronic prostatitis or CPPS. Similarly, a normal control (or reference control) level of PAA-specific T cells can readily be determined by determining the level of PAA-specific T cells in a statistically significant number of individuals who do not have CP/CPPS or who do not have an autoimmune response against PAA.

Various methods known in the art may be used to determine the level of an immune response, e.g., to determine the level of an antigen-specific antibody, to determine the level of antigen-specific T cells, etc. A biological sample obtained from a patient is analyzed. The biological sample for analysis can be seminal fluid, semen, blood, plasma, serum, or tissue biopsy sample (e.g., prostate biopsy sample). The sample is analyzed for indication of an immune response to a PAA. The immune response can be determined from the presence of, e.g., antibodies or T-cells that specifically bind to the PAA. The level of immune response may also be a measurement of inflammation, prostatitis symptoms, prostate specific antigens, antibodies against PAA, and anti-PAA T-cell response, e.g. CD4$^+$ response, CD8$^+$ response.

Where T cell responses are of interest, the sample is a sample comprising lymphocytes, e.g. seminal fluid, a blood sample, the cellular portion of a blood sample, etc. T cells can be stained with a peptide/MHC complex, for example using detectably labeled MHC reagents (i•TAg™ MHC Tetramers, Beckman Coulter; BD™ DimerX reagents; ProImmune Pro5® MHC class I Pentamers etc.) to determine the presence of T cells having specificity for a PAA. Alternatively, T cells may be assayed in vitro for reactivity to a PAA, using methods known in the art. For example, a sample comprising T cells may be contacted with a PAA presented by an antigen presenting cell (APC); or provided as a stable MHC complex; and the response of the cells quantitated, for example by proliferation, cytokine synthesis, cytotoxicity and the like. Measured values may thus include quantitation of PAA-specific T cells, quantitation of T cell proliferation in response to a PAA, quantitation of cytokine release, e.g. IFN-γ, IL-2, etc. in response to presented PAA, percentage of specific cell lysis of an APC presenting a PAA, and the like.

In some embodiments, diagnostic methods involve detecting the number of PAA-specific CD4$^+$ T cells in a biological sample obtained from an individual. The number of PAA-specific CD4$^+$ T cells can be determined using, e.g., a $^{51}$Cr release assay, where target cells pulsed with a PAA and labeled with $^{51}$Cr are contacted with a test sample that may contain PAA-specific CD4$^+$ T cells. The number of PAA-specific CD4$^+$ T cells is determined by measuring release of $^{51}$Cr from the target cells.

In certain embodiments, the level of an autoantibody, present in a biological sample from an individual who has prostatitis or from a test individual suspected of having prostatitis, to a PAA, is a measured value of an autoimmune response. If the level of PAA-specific autoantibody is substantially higher than a control level, this indicates that the prostatitis is caused by an autoimmune response against the PAA and also predicts an increased likelihood that the individual may exhibit a clinically beneficial response to treatment with an immunomodulatory treatment regimen. Autoantibodies to be detected that are specific for a PAA can include antibodies of any isotype; single-chain Fv; Fab; Fab; Fv; F(ab')$_2$; and the like. A biological sample obtained from an individual is contacted with PAA. If a significantly high level of autoantibodies from an individual form a complex with the PAA, it is an indication that an autoimmune response has been mounted in the individual and prostatitis may be diagnosed.

In other embodiments, an antibody profile is detected in a biological sample (e.g., seminal fluid, blood, or a blood product such as serum, plasma, etc.), and the antibody profile either correlates directly with or is inversely correlated with, the severity of the symptoms associated with prostatitis. It may also predict the level of a clinically beneficial response to treatment with an immunomodulatory treatment regimen.

In some embodiments, the level of autoantibody to two or more PAA is determined. For example, in some embodiments, the level of autoantibody to different isoforms or fragments of SG is determined. Where the level of autoantibody to two or more PAA is determined, the two or more antibody levels are collectively referred to as an "antibody profile."

Antibody profile of an individual who has prostatitis may be compared to the control antibody profile, e.g., profile obtained from an individual who does not have prostatitis in order to determine whether there is an autoimmune response that caused the prostatitis. The antibody profile may also help determine whether an immunomodulatory treatment may be beneficial to the individual with prostatitis.

In some embodiments, the level of an autoantibody is expressed as a "normalized level." For example, either Quantile Normalization or Robust Linear Normalization can be utilized to obtain a "normalized level". In one embodiment, Quantile Normalization is utilized to obtain a normalized response level. In the context of protein arrays, this method forces the arrays to have identical intensity distribution to allow comparison between arrays that may have systematic measurement errors.

In another embodiment, Robust Linear Normalization is utilized to obtain a normalized response level. This method uses a statistical linear model and positive control proteins, e.g., IgG and V5 to fit the model and also removes systematic measurement errors.

The level of an antibody to a PAA can be determined using any of a number of immunological assays. For example, a detectably labeled PAA, or a panel of detectably labeled PAA, can be employed, where the level of signal produced in such an assay is proportional to the amount of antibody in a biological sample. Suitable assays include, e.g., enzyme-linked immunosorbent assays (ELISA), radioimmunoassay (RIA), western blot, surface plasmon resonance, and the like.

In some embodiments, the assay is a sandwich assay, in which an antibody specific for the Fc portion of human antibody is immobilized on an insoluble support; a biological sample from a test individual (e.g., an individual having prostatitis; an individual having prostatitis who has been treated with an immunomodulatory treatment regimen; an individual suspected of having prostatitis) is contacted with the immobilized antibody, forming a complex between antibodies present in the biological sample and the immobilized antibody; and the complex is contacted with a detectably labeled PAS. The level of signal produced by the detectably labeled PAA indicates the level of antibody in the biological sample that is specific for a PAA. Suitable insoluble support materials include, e.g., agarose, sepharose, nitrocellulose, silica, polystyrene, and the like. The insoluble support can be in any of a variety of forms, including, e.g., beads, magnetic beads, films, strips, chips, multi-well plates, and the like.

In some embodiments, the outcome of a subject diagnostic method (e.g., whether an individual is considered to have CP/CPPS) is provided in a report. Thus, in some embodiments, a subject method further includes a step of preparing or generating a report that includes information regarding the results of the determining (e.g., assaying) step. For example, a subject method can further include a step of generating or outputting a report providing the results of the level of anti-PAA antibodies in the individual and/or the number of anti-PAA T cells in the individual, which report can be provided in the form of an electronic medium (e.g., an electronic display on a computer monitor), or in the form of a tangible medium (e.g., a report printed on paper or other tangible medium).

Monitoring Patient Response to Treatment for Chronic Prostatitis

The present disclosure provides methods of monitoring patient response to a treatment for CP/CPPS. The methods generally involve assaying the level of an immune response in an individual to a PAA at a first time point and at at least a second time, where the second time point is later than the first time point, and where the difference (if any) in the level of immune response to a PAA between the first time point and the second time point provides an indication as to whether the individual is responding to the treatment for CP/CPPS.

The first time point can be before treatment begins; and the at least second time point can be a time point after the beginning of treatment. For example, the first time point can be from one month to two weeks, from about two weeks to about one week, from about one week to about one day, from about one day to about 12 hours, from about 12 hours to about 1 hour, or less than one hour (e.g., 5 minutes to 15 minutes, 15 minutes to 30 minutes, or 30 minutes to about 60 minutes) before treatment for CP/CPPS begins. The second time point can be from about 12 hours to about 1 day, from about 1 day to about 1 week, from about 1 week to about 1 month, or more than 1 month, after treatment begins. The level of an immune response to a PAA can be assayed at additional time points, e.g., third, fourth, fifth, and further time points. The level of an immune response to a PAA can be assayed at substantially regular time intervals, e.g., once per week, one every two weeks, once a month, once every three months, etc., following the beginning of treatment for CP/CPPS.

In the context of disease prognosis, the level of autoimmune response against a PAA present in a biological sample from an individual who has prostatitis and who has undergone treatment with an immunomodulatory treatment regimen may be substantially lower than the level of the immune response in an individual before treatment with the immunomodulatory treatment regimen.

In other methods, a control value of immune response (e.g., a mean and standard deviation) is determined from a control population of individuals who have undergone treatment with a therapeutic agent. Measured values of immune response in a patient are compared with the control value. If the measured level in a patient is not significantly different (e.g., more than one standard deviation) from the control value, treatment can be discontinued. If the level in a patient is significantly above the control value, continued administration of the treatment regimen is warranted. If the level in the patient persists above the control value, then a change in treatment regimen can be indicated.

In other methods, a patient who is not presently receiving treatment but has undergone a previous course of treatment is monitored for immune response to determine whether a resumption of treatment is required. The measured value of immune response in the patient can be compared with a value of immune response previously achieved in the patient after a previous course of treatment. A significant decrease relative to the previous measurement (i.e., greater than a typical margin of error in repeat measurements of the same sample) is an indication that treatment is effective. Alternatively, the value measured in a patient can be compared with a control value (mean plus standard deviation) determined in a population of patients after undergoing a course of treatment. Alternatively, the measured value in a patient can be compared with a control value in populations of prophylactically treated patients who remain free of symptoms of disease, or populations of therapeutically treated patients who show amelioration of disease characteristics. In all of these cases, a significant increase relative to the control level (i.e., more than a standard deviation) is an indicator that treatment should be resumed in a patient.

Differential Diagnosis

The present disclosure further provides a method for differential diagnosis to distinguish between chronic (non-bacterial) prostatitis and prostate cancer (or benign prostate hyperplasia; BPH). A subject method of differential diagnosis generally involves assaying a level of an immune response to a PAA in an individual. In some embodiments, a subject method further involves assaying a level of prostate-specific antigen (PSA) in a biological sample (e.g., serum, plasma, blood, etc.) obtained from the individual. Where the level of PSA is higher than normal, and the level of anti-PAA immune response is normal, at least a provisional diagnosis of prostate cancer or BPH can be made, and additional test(s) for prostate cancer and/or BPH may be ordered. Where the level of PSA is higher than normal, and the level of anti-PAA immune response is higher than normal, a diagnosis of CP/CPPS can be made. Where the level of PSA is higher than normal, the level of anti-PAA immune response is higher than normal, and a diagnosis of CP/CPPS is made, more invasive diagnostic methods such as biopsy can be avoided. Where the level of PSA is higher than normal, the level of anti-PAA immune response is higher than normal, and a diagnosis of CP/CPPS is made, treatment for CP/CPPS may be indicated.

Levels of PSA less than 4 ng/mL are considered normal; levels of PSA between 4 ng/mL and 10 ng/mL are associated with a 20-30% risk of prostate cancer; levels of PSA between 10 ng/mL and 20 ng/mL are associated with a 50-75% risk of prostate cancer; and levels of PSA greater than 20 ng/mL are associated with a 90% risk of prostate cancer.

Methods of determining the level of PSA in a biological sample (e.g., blood; serum; plasma; etc.) are well established in the art. Any known method can be used in conjunction with a subject method of differential diagnosis. Typically, the assay is an immunological assay employing antibody specific for PSA. See, e.g., U.S. Pat. No. 7,045,605; U.S. Pat. No. 6,107,049; U.S. Pat. No. 6,361,955.

In some embodiments, the outcome of a subject differential diagnostic method (e.g., whether an individual is considered to have CP/CPPS or whether an individual is considered to have prostate cancer or BPH) is provided in a report. Thus, in some embodiments, a subject method further includes a step of preparing or generating a report that includes information regarding the results of the determining (e.g., assaying) step. For example, a subject method can further include a step of generating or outputting a report providing the results of the level of anti-PAA antibodies in the individual and/or the number of anti-PAA T cells in the individual and/or the level of PSA in the individual, which report can be provided in the form of an electronic medium (e.g., an electronic display on a computer monitor), or in the form of a tangible medium (e.g., a report printed on paper or other tangible medium).

Evaluating Basis of Male Sterility

The present disclosure further provides a method for evaluating the basis for male sterility in a male. The method generally involves assaying a level of an immune response to a PAA in a male individual. Where the results of the assay indicate a higher than normal (or reference) level of immune response to PAA, the cause of male sterility can be attributed to CP/CPPS. Treatment for CP/CPPS can then be prescribed.

Assessing Likelihood of Response to Treatment

The present disclosure provides methods of assessing the likelihood that a patient having prostatitis will exhibit a beneficial response to treatment with an immunomodulatory treatment regimen. Patients subject to such an assessment include: patients who have symptoms of chronic prostatits, CPPS, non-infectious chronic prostatitis, or who have an elevated levels of PSA. Patients may also include those who have been treated with an immunomodulatory treatment regimen or who may be subjected to an immunomodulatory treatment.

For example, the level in an individual who has prostatitis (and who has not yet been treated for the prostatitis) of an antibody against one or more PAA that is at least about 25%, at least about 50%, at least about 75%, at least about 100% (or two-fold), at least about 2.5-fold, at least about 5-fold, at least about 10-fold, at least about 25-fold, at least about 50-fold, or at least about 100-fold higher than a normal control level of antibody (e.g., in an individual without prostatitis or without an autoimmune response), indicates that the cause of prostatitis may be due to an autoimmune response against semenogelin proteins. It also indicates an increased likelihood that the individual will exhibit a clinically beneficial response to treatment with an immunomodulatory treatment regimen.

For example, the level in an individual who has prostatitis (and who has not yet been treated for the prostatitis) of an antibody against one or more target antigens that is at least about 25%, at least about 50%, at least about 75%, at least about 100% (or two-fold), at least about 2.5-fold, at least about 5-fold, at least about 10-fold, at least about 25-fold, at least about 50-fold, or at least about 100-fold higher than a normal control level of antibody may predict an at least about 10%, at least about 20%, at least about 25%, at least about 30%, at least about 35%, at least about 40%, at least about 45%, at least about 50%, at least about 60%, at least about 70%, at least about 80%, or greater than 80%, increased likelihood that the individual will exhibit a clinically beneficial response to treatment with an immunomodulatory treatment regimen.

Diagnostic Kits

The present disclosure further provides kits for use in any of the above-mentioned diagnostic methods. Such kits typically comprise two or more components necessary for performing a diagnostic assay for the detection of immune responses specific to a prostatitis-associated target antigen. Components can be compounds, reagents, containers and/or equipment. Kits also typically contain labeling providing directions for use of the kit. For example, one container within a kit can contain one or more fragments or a full-length prostatitis-associated target antigen. Alternatively, the target antigens may be provided attached to a support material. One or more additional containers can enclose elements, such as reagents or buffers, to be used in the assay. Such kits can also, or alternatively, contain a detection reagent that contains a reporter group suitable for direct or indirect detection of antibody binding. For example, secondary antibodies to recognize antibodies, e.g. human IgG, may be provided. The term labeling refers to any written or recorded material that is attached to, or otherwise accompanies a kit at any time during its manufacture, transport, sale or use. For example, the term labeling encompasses advertising leaflets and brochures, packaging materials, instructions, audio or video cassettes, computer discs, as well as writing imprinted directly on kits.

In certain cases, a subject kit comprises a subject target antigen immobilized on a solid support and a labeled reagent capable of binding to an antibody specific for the subject target antigen.

PAA-Specific Antibodies

The present disclosure provides antibodies specific for a subject PAA. In certain embodiments, a subject PAA-specific antibody is isolated, e.g., is in an environment other than its naturally-occurring environment. Suitable antibodies specific for a PAA include antibodies of any isotype; single-chain Fv; Fab; Fab; Fv; F(ab')$_2$; artificial antibodies; humanized antibodies; and the like. In some embodiments, a subject antibody is specific for a mutant prostate-associated target antigen.

Suitable antibodies are obtained by immunizing a host animal with peptides comprising all or a portion of a subject prostate cancer-associated target antigen. Suitable host animals include mouse, rat sheep, goat, hamster, rabbit, etc. The host animal will generally be from a different species than the immunogen where the immunogen is from a naturally occurring source, e.g., a human sample, where representative host animals include, but are not limited to, e.g., rabbits, goats, mice, etc.

In certain embodiments, the antibodies specific for target antigens may be useful in determining the essential epitopes on the target antigens. Antibody profiles to different fragments of SG or other SVS2-related proteins may help pinpoint the portion of the SG or SVS2-related protein that is immunogenic. The immunogenic portion of the SG or SVS2-related protein may also contain an epitope for autoantibodies developed in an individual with an autoimmune response. If the autoantibody-specific epitopes of SG or SVS2-related proteins are known, the immunogenic composition and the method of the present disclosure may employ such immunogenic fragments containing such epitopes instead of a larger or full-length SG.

A subject anti-PAA antibody will in some embodiments comprise an anti-cancer agent for delivery to a site of a cancer cell to further facilitate tumor killing or clearance. The anticancer agent can be attached covalently or non-covalently, directly or via a linker, to the anti-PAA antibody. Suitable anti-cancer agents that can be attached to a subject anti-PAA antibody include, but are not limited to, an anti-proliferation moiety (e.g., vascular endothelial growth factor (VEGF) antagonist); a toxin (e.g., an anti-cancer toxin, e.g., ricin, *Pseudomonas* exotoxin A, and the like); a radionuclide (e.g. $^{90}Y$, $^{131}I$, $^{177}L$, $^{10}B$, and the like), anti-cancer drugs (e.g. doxorubicin, 5-fluorouracil, leucovorin, a taxane (e.g., docetaxel, paclitaxel), mitozantrone, vinblastine, estramustine phosphate, etoposide, etc.), and/or can optionally be modified to provide for improved pharmacokinetic profile (e.g., by PEGylation (e.g., attachment of one or more poly(ethylene glycol) moieties), hyperglycosylation, and the like). A subject anti-PAA antibody can comprise, attached thereto, a ribosome inactivating protein (RIP), a photo-activatable cytotoxin, a vinca alkaloid, an anthracycline, an invertebrate toxin, or a bacterial toxin.

Methods of Treating Prostatitis

The present disclosure provides methods of treating CP/CPPS in an individual having CP/CPPS, the methods generally involving administering to the individual an agent in an amount effective to decrease the level of an anti-PAA immune response.

In some embodiments, an effective amount of an agent is an amount that is effective, when administered in one or more doses, to reduce the level of autoantibodies against PAA and/or the amount of T cell response against PAA in an individual by at least about 10%, at least about 20%, at least about 25%, at least about 30%, at least about 40%, at least about 50%, at least about 60%, at least about 70%, at least about 80%, or more than 80%, compared to the level of anti-PAA antibody or PAA-specific T cells in the individual not treated with the agent.

A subject treatment regimen includes an "immunomodulatory treatment regimen," involving administration to an individual of an effective amount of an agent that reduces an autoimmune response to a PAA in an individual. Immunomodulatory treatment regimens for the treatment of prostatitis include any treatment that modulates an immune response in the individual such that an autoimmune response to a PAA is reduced.

In some embodiments, immunomodulatory agents include inhibitors of T cells, such as small molecule inhibitors, oligonucleotide inhibitors, or peptide inhibitors. The agent may be immunosuppressants directed against T cells. In certain cases, the immunosuppressant may be directed specifically against CD4$^+$ T cells. In certain embodiments, the immunosuppressive effect may be initiated by inhibiting cyclin-dependent kinases or Src kinases. See Singh RP et al. (2008) Inflamm Allergy Drug Targets 7:253-9, Lopez-Diego (2008) Nat Rev Drug Discov. 7: 909-25, and Javeed et al. (2008) Mol Diagn Ther. 12: 171-81 for more details on immunomodulatory agents.

In some embodiments, "an immunomodulatory treatment regimen" includes treatment with two or more agents, one or more of which is an immunomodulatory agent.

In some embodiments, an immunomodulatory treatment regimen comprises administration of an agent that increases the activity and/or level of PAA-specific Tregs in an individual. For example, in some embodiments, an agent is administered that increases the level of PAA-specific CD4$^+$ Foxp3$^+$ regulatory T cells in an individual.

In some embodiments, an effective amount of an agent is an amount that, when administered in one or more doses, results in an at least about 5%, at least about 10%, at least about 15%, at least about 20%, at least about 25%, at least about 30%, at least about 40%, at least about 50%, at least about 60%, at least about 70%, at least about 80%, at least about 90%, or more than 90%, reduction in the level of anti-PAA immune response in the individual before treatment with the agent.

In some embodiments, an effective amount of an agent is an amount that, when administered in one or more doses, results in an at least about 5%, at least about 10%, at least about 15%, at least about 20%, at least about 25%, at least about 30%, at least about 40%, at least about 50%, at least about 60%, at least about 70%, at least about 80%, at least about 90%, or more than 90%, reduction in the severity of one or more symptoms of CP/CPPS in the individual, compared to the severity of the one or more symptoms in the absence of treatment with the agent.

Methods of Treating Prostate Cancer and/or Benign Prostatic Hyperplasia

The present disclosure provides methods of treating prostate cancer, and methods of treating benign prostatic hyperplasia (BPH). The methods generally involve administering to an individual in need thereof an effective amount of a PAA. In some embodiments, the methods involve administering to an individual in need thereof an effective amount of a subject immunogenic composition. In some embodiments, the methods involve administering to an individual in need thereof an effective amount of a subject PAA-specific antibody, e.g., a subject PAA-specific antibody that comprises an anti-cancer agent attached thereto.

Whether a subject method is effective to treat prostate cancer can be determined using any known method, e.g., measuring levels of PSA in a biological sample from the individual; analyzing a biopsy sample from a prostate tumor to determine the number of cancer cells; measuring the size of the prostate tumor; carrying out an imaging method (e.g., ultrasound, computed tomography, magnetic resonance imaging) to assess the size of the tumor; etc.

Administering a PAA

In some embodiments, an effective amount of a PAA (or an immunogenic composition comprising a PAA) is an amount that induces an immune response to a PAA in the individual, where the immune response is effective to achieve one or more of: reducing the growth rate of prostate cancer in an individual, reducing the size of a prostate tumor in an individual, and reducing the number of prostate cancer cells in the individual. In some embodiments, an effective amount of a PAA (or an immunogenic composition comprising a PAA) is an amount that is effective to induce a T cell response to a prostate cancer cell, e.g., to induce a T cell response to a cell surface antigen present on a prostate cancer cell. T cell responses include cytotoxic T cell responses (e.g., $CD8^+$ T cell responses), $CD4^+$ T cell responses, etc.

For example, in some embodiments, an effective amount of a PAA (or an immunogenic composition comprising a PAA) is an amount that is effective, when administered in one or more doses, to reduce the number of prostate cancer cells in an individual by at least about 10%, at least about 20%, at least about 25%, at least about 30%, at least about 40%, at least about 50%, at least about 60%, at least about 70%, at least about 80%, or more than 80%, compared to the number of prostate cancer cells in the untreated individual.

In some embodiments, a PAA, or an immunogenic composition comprising a PAA, is administered as a single dose. In other embodiments, a PAA, or an immunogenic composition comprising a PAA, is administered in multiple doses, e.g., a first dose, followed by one or more booster doses.

A PAA, or an immunogenic composition comprising a PAA, can be administered via various enteral and parenteral routes of administration, where parenteral routes of administration include intramuscular, intravenous, subcutaneous, and the like, and where enteral routes of administration include oral, buccal, rectal, etc. A PAA can be administered as a bolus or by continuous infusion over a period of time, by intramuscular, subcutaneous, intravenous, oral, intratumoral, peritumoral, intralesional, or perilesional routes, to exert local as well as systemic therapeutic effects.

A PAA, or a subject immunogenic composition comprising a PAA, is administered to an individual in one or more doses. Suitable amounts of a PAA per dose range from about 100 μg to about 100 mg, e.g., from about 100 μg to about 250 μg, from about 250 μg to about 500 μg, from about 500 μg to about 1 mg, from about 1 mg to about 10 mg, from about 10 mg to about 25 mg, from about 25 mg to about 50 mg, from about 50 mg to about 75 mg, or from about 75 mg to about 100 mg.

Suitable dosage forms encompass pharmaceutically acceptable carriers that are inherently nontoxic and nontherapeutic. Examples of such carriers include ion exchangers, alumina, aluminum stearate, lecithin, serum proteins, such as human serum albumin, buffer substances such as phosphates, glycine, sorbic acid, potassium sorbate, partial glyceride-mixtures of saturated vegetable fatty acids, water, salts, or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, and polyethylene glycol. Other carriers include polysaccharides such as sodium carboxymethylcellulose or methylcellulose, polyvinylpyrrolidone, polyacrylates, polyoxyethylene-polyoxypropylene-block polymers, polyethylene glycol, and wood wax alcohols. Conventional depot forms are suitably used. Such forms include, for example, microcapsules, nano-capsules, liposomes, plasters, tablet, capsules, etc.

Administering a PAA-Specific Antibody

In some embodiments, the methods involve administering to an individual in need thereof an effective amount of a subject PAA-specific antibody. The PAA-specific antibody is administered in one or more doses, as described above for administration of PAA. In some embodiments, a subject method involves administering a subject PAA-specific antibody that comprises an anti-cancer agent attached thereto. A PAA-specific antibody can be administered in a composition together with one or more pharmaceutically acceptable carriers, as described above for administration of PAA.

In some embodiments, an effective amount of an anti-PAA antibody is an amount that is effective, when administered in one or more doses, to reduce the number of prostate cancer cells in an individual by at least about 10%, at least about 20%, at least about 25%, at least about 30%, at least about 40%, at least about 50%, at least about 60%, at least about 70%, at least about 80%, or more than 80%, compared to the number of prostate cancer cells in the untreated individual.

Combination Therapy

In some embodiments, a subject method of treating prostate cancer or BPH involves combination therapy, e.g., administering an effective amount of a PAA (or an effective amount of a subject immunogenic composition comprising a PAA) and administering at least one additional therapy to treat the prostate cancer or BPH, where suitable additional therapies include, e.g., surgical treatment, radiation therapy, hormone therapy, and chemotherapy.

Surgical treatments that can be carried out in conjunction with a subject combination therapy include, but are not limited to, prostatectomy and orchiectomy. Radiation therapy that can be carried out in conjunction with a subject combination therapy includes, but is not limited to, external beam radiation therapy, intensity-modulated radiation therapy, and brachytherapy. Hormone therapy that can be carried out in conjunction with a subject combination therapy includes, but is not limited to, androgen-deprivation therapy; administration of a leuteinizing hormone releasing hormone (LHRH) agonist (e.g., leupropride, goserelin, triptorelin); administration of an anti-androgen (e.g., bicalutamide, flutamide, nilutamide); and the like. Chemotherapy that can be carried out in conjunction with a subject combination therapy includes, but is not limited to, administration of one or more of a taxane (e.g., docetaxel, paclitaxel), mitozantrone, doxorubicin, vinblastine, estramustine phosphate, and etoposide.

Subjects Suitable for Diagnosis and/or Treatment

Individuals who are to be diagnosed using a subject diagnostic method include male individuals (e.g., mammals, including humans). Such individuals include males who are suspected of having CP/CPPS (e.g., non-bacterial prostatitis). Such individuals also include individuals who have undergone a test for PSA levels, and who have exhibited higher than normal levels of PSA, where such individuals include males who have serum PSA levels higher than 4 ng/mL, e.g., from about 4 ng/mL to about 10 ng/mL, from about 10 ng/mL to about 20 ng/mL, or greater than 20 ng/mL. Individuals who are to be diagnosed using a subject diagnostic method include males from 10 years to 12 years, from 13 years to 18 years, from 18 years to 25 years, from 25 years to 30 years, from 30 years to 40 years, from 40 years to 50 years, from 50 years to 60 years, or from 60 years to 70 years, in age, or older than 70 years.

Individuals who are to be diagnosed using a subject differential diagnostic assay include male individuals who have had a rectal digital examination and who are considered to possibly have prostate cancer; male individuals who have undergone a test for PSA levels, and who have exhibited higher than normal levels of PSA, where such individuals include males who have serum PSA levels higher than 4 ng/mL, e.g., from about 4 ng/mL to about 10 ng/mL, from about 10 ng/mL to about 20 ng/mL, or greater than 20 ng/mL. Individuals who are to be diagnosed using a subject differential diagnostic method include males from 10 years to 12 years, from 13 years to 18 years, from 18 years to 25 years, from 25 years to 30 years, from 30 years to 40 years, from 40 years to 50 years, from 50 years to 60 years, or from 60 years to 70 years, in age, or older than 70 years.

Individuals who are suitable for treatment with a subject method of treating prostatitis include male individuals who have a higher than normal level of anti-PAA antibody and/or T cell response, e.g., who have a level of anti-PAA antibody and/or a level of anti-PAA T cells that is at least about 10%, at least about 15%, at least about 20%, at least about 25%, at least about 30%, at least about 40%, at least about 50%, at least about 75%, at least about 100% (or 2-fold), at least about 2.5-fold, at least about 3-fold, at least about 4-fold, at least about 5-fold, at least about 10-fold, at least about 25-fold, or at least about 50-fold, or more than 50-fold, higher than a normal control level of anti-PAA antibody and/or anti-PAA T cells. Individuals, who exhibit higher than normal levels of anti-PAA antibody and/or higher than normal levels of anti-PAA T cells, that are suitable for treatment with a subject method include males from 10 years to 12 years, from 13 years to 18 years, from 18 years to 25 years, from 25 years to 30 years, from 30 years to 40 years, from 40 years to 50 years, from 50 years to 60 years, or from 60 years to 70 years, in age, or older than 70 years.

Individuals who are suitable for treatment with a subject method of treating prostate cancer or BPH include male individuals (e.g., human males) who have been diagnosed with prostate cancer or BPH; male individuals (e.g., human males) who are considered at greater risk of developing prostate cancer or BPH compared to normal control individuals or compared to the general male population; male individuals (e.g., human males) who have been treated for prostate cancer and who failed to respond to such treatment; and male individuals (e.g., human males) who have been treated for prostate cancer, who responded to the treatment, but in whom the prostate cancer recurred.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

Example 1

Role of Prostate Antigen-Specific Immune Response in Prostatitis

Materials and Methods
Mice and Reagents

Aire-KO mice were generated as previously described in Penna, G. et al. (2007) *Eur Urol* 51:524-533. Aire-KO male mice used in these experiments were backcrossed into the C57BL/6 (B6) and NOD Lt/J backgrounds>10 generations and generated using heterozygous breeders. WT B6 mice used in the experiments were littermates of the Aire-KO mice. C57BL/6×NOD Lt/J F2 Aire-deficient mice were derived from intercrosses of C57BL/6 and NOD Lt/J Aire-KO mice. All mice were housed in a pathogen-free barrier facility at the UCSF. Experiments complied with the Animal Welfare Act and NIH guidelines for the ethical care and use of animals in biomedical research and were approved by the UCSF Animal Care and Use Committee. Tissue culture experiments were performed in RPMI 1640 media (Cambrex, Walkersville, N.J.) supplemented with 10% fetal calf serum (Cambrex, Walkersville, N.J.), penicillin/streptomycin (Sigma, St. Louis, Mo.) and non-essential amino acids (Cambrex, Walkersville, N.J.).

Antigens

The natural mouse SVS2 and human SG were purified from mouse and human semen plasma, respectively, based on the method described previously (Malm, J. et al., (1996) *Eur J Biochem* 238:48-53). In brief, fresh seminal plasma were collected in a 40 mmol/l Tris/HCL buffer pH9.7 with 4M urea, 25 mmol/l EDTA, 30 mmol/l DTT, 3 mmol/l benzamidine and 0.5 mmol/l Pefabloc (Boehringer, Ridgefield, Conn.) at 4° C., and was applied on a heparin-sepharose column (0.7×2.5 cm, GE Healthcare, Pittsburgh, Pa.) that was equilibrated with 0.1 mol/l Tris pH8.5, 2M urea, 5 mmol/l EDTA, 3 mmol/l DTT, 3 mmol/l benzamidine and 0.2 mmol/l Pefabloc buffer. Following application of the sample, the column was washed with 5×2 ml of equilibration buffer then 4 ml of 0.1M NaCl. The column was eluted with 4 ml of 0.25M NaCl buffer. The eluant was desalted and concentrated with 30 Kd cut-off Centricons (Millipore, Billerica, Mass.). The recombinant MBP-SVS2 and MBP-SG1 proteins were made as described in pMal Protein Fusion and Purification System's protocol from New England Biolabs Inc. with the following modifications. SVS2 gene that was cloned from mouse prostate and SG1 gene that was cloned from human prostate biopsy were subcloned in frame with MBP and transformed into Top Ten competent cells. Plasmid DNA isolated was transformed into BL21 (DE3)pLysS bacteria to express the fusion protein. Eluted proteins were concentrated with the Amicon Centricon columns with a 10-kD cutoff and washed 2 times with PBS. For ELISPOT assays, purified MBP, MBP-SVS2 and MBP-SG1 proteins were passed through a ProteoSpin endotoxin removal kit (Norgen Biotek Corp. Thorold, Canada). Protein concentrations were measured with BioRad Dc assay (BioRad, Hercules, Calif.) using BSA as the standard.

Immunoprecipitation

Immunoprecipitation of autoantigens was performed using protein G agarose coupled to Aire-sufficient or Aire-KO sera as described previously (Harlow, E., and Lane, D. 1999. Using antibodies: A lab manual. 495). In brief, whole prostate tissues were homogenized in 0.15 M NaCl, 0.05 M Tris (pH 8), and 0.1% CHAPS (Sigma, St. Louis, Mo.). Protein agarose G-coupled columns were washed in 30 mL PBS, and prostate extracts from RAG−/− mice prepared in CHAPS buffer were passed through the matrix. Columns were washed with 30 mL PBS and washed again with 30 mL of 10 mM phosphate, pH 6.8. Eluates were collected by passing 0.5 ml of 100 mM glycine, pH 2.5, over the column and collecting the flow through. Eluates from multiple runs were pooled and concentrated in a centrifugal protein concentrator (Vivaspin; Sartorius, UK).

In-Gel Digestion and PMF

SVS2 was identified by provisional peptide mass fingerprinting (PMF) as previously described in DeVoss, J. et al. (2006) *J Exp Med* 203:2727-2735. In brief, gel bands were excised, destained (stain-stripped) three times in 50% acetonitrile and 25 mM ammonium bicarbonate (pH 8), dehydrated with 100% acetonitrile, and dried in a Speed-Vac (Savant). Gel pieces were digested for 16 h at 37° C. Peptides were extracted, and PMF was used for preliminary protein identification. Mass spectra were produced by MALDI-TOF representing protonated molecular ions (MH$^+$) of tryptic peptides from the proteins present in each gel spot. The mass spectra were internally mass calibrated using two trypsin autolysis products present in the digest mixture. Preliminary protein identities were established by matching the experimentally determined peptide masses to those produced by an in silico tryptic digestion of the Swiss-Prot protein database (available at the ExPASy proteomics server of the Swiss institute of Bioinformatics) within the window of experimental mass measurement accuracy. The PMF data-searching algorithm (available through MS-Fit at the website: prospector.ucsf.edu) was used to perform the database searches.

Immunoblotting

Mouse or human sera were screened for the presence of autoantibodies by Western blotting. Rabbit anti-human SG antibody (Santa Cruz Biotechnology, Santa Cruz, Calif.) was used as a positive control. Secondary Goat anti-mouse, Goat anti-rabbit HRP antibody (Upstate, Billerica, Mass.) and Goat anti-human IgG HRP antibody (Invitrogen, Carlsbad, Calif.) were used in the respective assays. The resulting films developed with either Upstate Visualizer or ECL chemiluminescent substrate. For competition studies, C57BL/6×NOD DB F2 Aire-KO sera was preincubated with serial dilutions of either recombinant MBP-SVS2 or control MBP protein in TBS-T with 1% nonfat dry milk for 2 h at room temperature before use as the primary reagent to blot the membranes. The concentrations of protein used in these experiments were 30, 7.5, 1.88, 0.47 mcg.

Real-Time PCR

Real-time PCR was performed on cDNA prepared from DNase-treated RNA that were derived from the tested tissues or the CD45 negative thymic stroma cells that were purified by FACS sorting according to the previous method (Gray, D. H. et al., (2002) *J Immunol Methods* 260:15-28). Aire and cyclophilin specific-primers and probes were used as previously described (DeVoss, J. et al., (2006) *J Exp Med* 203: 2727-2735). SVS2 taqman primers/Fam-labeled MGB probes (Mn01251795_g1) were purchased from Applied Biosystems (Foster City, Calif.). Reactions were run on the HT7900 sequence detection system (Applied Biosystems).

ELISPOT Analysis

Mouse splenocytes were harvested from Aire-KO, WT B6 mice, or immunized WT B6 mice. Human PBMC was generated from a CPPS individual and a normal donor. The release of IFN-γ was measured by ELISPOT assay. Briefly, Multiscreen HTS IP plates (Millipore, Billerica, Mass.) were coated overnight with 2 µg/ml of anti-mouse IFN-γ mAb or anti-human IFN-γ mAb (BD Biosciences, San Diego, Calif.) at 4° C. The plates were washed with PBS and blocked with RPMI medium containing 10% FCS for 2 h at 37° C. Mouse splenocytes or human PBMC were added to each well with the different antigens and incubated for 18 hour in RPMI complete medium. The plates were washed with PBS before adding 2 µg/ml of biotin-labeled anti-mouse or anti-human IFN-γ mAb (2 µg/ml; BD Biosciences) respectively and incubated overnight at 4° C. After washing and further incubation with avidin-horseradish peroxidase (1:100 dilutions; BD Biosciences) for 1 h at room temperature, the plates were washed and developed using substrate solution (AEC; BD Biosciences, San Diego, Calif.). Positive spots displayed in the plate membranes were examined using an automated ELISPOT reader (AID; Autoimmun Diagnostika GmbH, Strassburg, Germany). The number of spot-forming cells was the average number of spots in duplicate or triplicate wells.

Generation of Antigen-Specific T Cell Lines

Aire-KO B6 male mice were immunized with the purified SVS2 (200 µg/mouse) emulsified in an equal volume of CFA (Difco). The antigens were injected s.c. into the foot pads. Mice were boosted twice with the same amount of antigen emulsified in IFA at 10 days intervals. 10 days following the second boost, single-cell suspensions from draining lymph nodes of SVS2-immunized mice were incubated with purified SVS2 (50 µg/ml). Twenty-four hours later, mouse IL-2 (50 u/ml), IL-7 (10 ng/ml) and IL 15 (10 ng/ml) (Peprotech) were supplemented into the media. Subsequent restimulations occurred at weekly intervals by the addition of purified SVS2-pulsed, irradiated B6 splenocytes to the cultures followed by the same cytokine supplementation 24 hours later. The OVA-specific T cell lines were generated in parallel in separate mice through the same procedure. After two cycles of restimulation, the dead cells were removed by centrifugation with ficoll (Histopaque-1083, Sigma), and the cultured cells were harvested for further analysis and adoptive transfer experiments.

Intracellular Cytokine Staining of Antigen-Specific T Cells

Antigen-specific T cell lines were incubated with the irradiated B6 splenocytes pulsed with MBP-SVS2 (50 µg/ml) for 24 hours. GolgiStop buffer (BD Biosciences) was added at a final concentration of 1 µg/ml for the last 4 hours of incubation. The cells were then harvested for intracellular cytokine staining. Briefly, the cells were first stained with anti-mouse CD4-APC antibody (BD Biosciences) and fixed with 4% formaldehyde in PBS for 10 min. Followed by being permeabilized with 1× BD perm/wash buffer (BD Biosciences) for 15 min, the cells were stained with anti-mouse IFN-γ-PE (eBioscience), anti-mouse IL 10-PE (Biolegend), or anti-mouse IL17a-FITC (BD Biosciences) antibodies. The cells were assessed by flow cytometry and analyzed with Flowjo (TreeStar).

Adoptive Transfer Experiment

Splenocytes were harvested from either B6 Aire-KO mice or immunized B6 mice. CD4+ or CD8+ T cells or CD19+ B cells were depleted using FACS sorting. Briefly, cells were stained with anti-CD4-PE, anti-CD8-PE or anti-CD19-PE antibodies (BD Pharmingen) for 30 min on ice, and then the PE negative cells (CD4+ depleted cells, CD8+ depleted cells and CD19+ depleted cells) were collected (FACSAria, BD, San Diego, Calif.). 5×106 sorted cells (CD4+ depleted, CD8+ depleted or CD19+ depleted) were injected i.v. into B6-RAG−/− mice. Animals were aged 40 days after the transfer, sacrificed, and analyzed.

SVS2 Immunization Experiments

B6 Male mice at 25-weeks of age were immunized s.c. with the recombinant MBP-SVS2 fusion protein (200 µg/mouse) or MBP (200 µg/mouse) as the control. Both proteins were emulsified in an equal volume of CFA (Difco, Lawrence, Kans.) supplemented with *mycobacterium tuberculosis* H37Ra. The antigens were injected S.C. on the back. Mice were boosted twice with the same amount of antigen emulsified in IFA at 2-week intervals. Two weeks following the second boost, tissues and sera were harvested for further analysis or adoptive transfer experiments.

Histopathology

For histology staining, prostate tissues were either fixed in 10% neutral buffered formalin and embedded in paraffin or frozen in OCT (Tissue Tek) tissue embedding compound at −80 C. After sectioning, tissues were stained with hematoxylin and eosin (Sigma, St. Louis, Mo.). For immunohistochemical staining, prostates were snap-frozen in OCT (Tissue Tek), sectioned at 6 um thick, and processed for staining using Vectastain Elite ABC Kit (Vector, Burlingame, Calif.) with biotinylated anti-rat AB against rat anti-mouse CD3 (clone CT-CD3; Caltag Laboratories, Carlsbad, Calif.), CD4 (clone H129.19; BD Pharmingen), CD8a (clone 53-6.7; BD Pharmingen), CD19 (clone 1D3; BD Pharmingen), followed by streptavidin-peroxidase conjugate. Colorimetric detection was visualized by using DAB substrate (Pierce, Rockford, Ill.). Histology was assessed by a pathologist, who scored lymphocytic infiltrates while blinded to mouse phenotype or treatment. The presence of inflammatory cells was scored by a pathologist according to the following categories: no infiltration, rare scattered inflammatory cells, obvious scattered cells without confluence, confluent sheets of cells and/or epithelial injury by inflammatory cells.

Human Subjects

Sera were obtained from consenting patients with clinical histories of CPPS as part of an IRB-approved protocol at the University of Washington Medical Center. Clinical assessment of prostatitis in the prostate biopsies was performed by the pathology department. Control sera were obtained from male volunteer blood donors without histories of prostatitis symptoms. Sera were stored in aliquots at −80° C. until used.

Statistical Analysis

For the mouse study, differences between groups were evaluated using two-tailed Student's T test. Differences were considered to be statistically significant at p<0.05. For human studies, differences between groups were evaluated by Fishers exact test. Differences were considered to be statistically significant at p<0.05.

Results

Role of Prostate-Associated Antigen in Prostatitis

Aire-KO mice spontaneously develop multi-organ autoimmunity, including those of the eye, salivary glands, ovaries and stomach. Inflammation in the prostate was also observed in most Aire-KO mice, but the nature of immune recognition for autoimmune prostatitis in Aire-KO mice had not been reported. Histological experiments were carried as detailed below in order to confirm the pathology of prostate in Aire-KO mice.

Histological changes in the prostates of Aire-KO mice were examined in the staining of representative prostate sections from Aire-KO and Aire-sufficient (WT) mice. In Aire-KO mice, the inflammation seen included cellular extravasation into the interstitial tissue between the glands as well as infiltration into glandular epithelium of both the dorsal and ventral prostate glands leading to effacement of the usual glandular architecture in severe cases (FIG. 1A; the urethra (u) and ductus deferens (dd), two ducts that course through the prostate glands are denoted; upper panels: 4× magnification; lower panels: 40× magnification). Moderate to severe prostate inflammation, including intraepithelial infiltration of prostate glands by lymphocytes, was observed in 5 of 7 examined male C57BL/6 Aire-KO mice at 10-20 weeks of age, but completely absent in all of the 5 Aire-wild-type (WT) littermate controls (18-20 wk old) (FIG. 1B) (Table 2). Scoring was performed blindly by a pathologist using a scoring system adapted from grading used in evaluating human prostate tissues (p<0.001, unpaired Student's T-test). Immunohistochemistry performed on Aire-KO prostate glands demonstrated a predominance of CD4+ T cells among the infiltrating cells in the prostates (FIG. 1C, upper panels). The staining was performed for CD4, CD8, CD19 and anti-rat IgG in cryostatic sections of prostates from a representative 20 week-old Aire-KO (upper panel) and WT (lower panels) mice. Staining is representative of 6 Aire-KO mice and 5 WT mice. CD8+ T cells were observed but in fewer numbers than CD4+ T cells. Nevertheless both CD4+ and CD8+ T cells could be seen infiltrating the glandular epithelia of these prostates. CD19+ B cells were seen at low frequency, and if present, resided within the stroma of the prostate tissue. In contrast, wild-type mice lacked lymphocytes within either the glandular cell layer or the stroma (FIG. 1C, lower panels).

TABLE 1

Histologic score of inflammatory inflitrates

| | Pathology Score | | | | |
|---|---|---|---|---|---|
| | 0 | 1 | 2 | 3 | 4 |
| Mononuclear Infiltration in Glands | − | − | + | ++ | +++ |
| Mononuclear Infiltration in Stroma | − | + | any | any | +++ |

"−", no infiltration;
"+", rare scattered inflammatory cells;
"++", obvious scattered cells without confluence;
"+++", confluent sheets of cells and/or epithelial injury by inflammatory cells (replacing or destroying mucosal cells).

FIGS. 1A-C. Spontaneous Development of Autoimmune Prostatitis in the Aire-KO Mouse.

(A) H&E staining of representative prostate sections from Aire-KO and Aire-sufficient mice (WT). The urethra (u) and ductus deferens (dd), two ducts that course through the prostate glands are denoted. Upper panels: 4× magnification; lower panels: 40× magnification. (B) Mononuclear infiltration in H&E stained prostate sections from 7 Aire-KO and 5 Aire-sufficient (WT) littermate mice on C57BL/6 background (18-20 wk old) was graded blindly by a pathologist using a scoring system adapted from grading used in evaluating human prostate tissues (Suppl. Table 1). p<0.001, unpaired Student's T-test. (C) Immunohistochemical staining for CD4, CD8, CD19 and anti-rat IgG in cryostatic sections of prostates from a representative 20 week-old Aire-KO (upper panel) and WT (lower panels) mice. Staining is representative of 6 Aire-KO mice and 5 WT mice.

Aire-KO Mouse Develop Spontaneous Immune Responses to SVS2.

In order to define the relevant prostate autoantigens that mediate this prostatitis, sera of Aire-KO mice were screened for autoantibodies to proteins present in the protein lysates derived from mouse prostate tissue.

Sera of Aire-deficient and WT mice were used in western blots to determine whether autoantibodies were present. Immunoblotting of whole prostate extracts was performed with the sera from male Aire-deficient and WT mice on the B6/NOD F2 background (individual mice listed by number). Each lane of the multi-screen immunoblot represents the reactivity of sera from individual mice. Gel bands stained by sera from multiple Aire-KO mice were excised and analyzed by mass spectroscopy.

Figure 2:
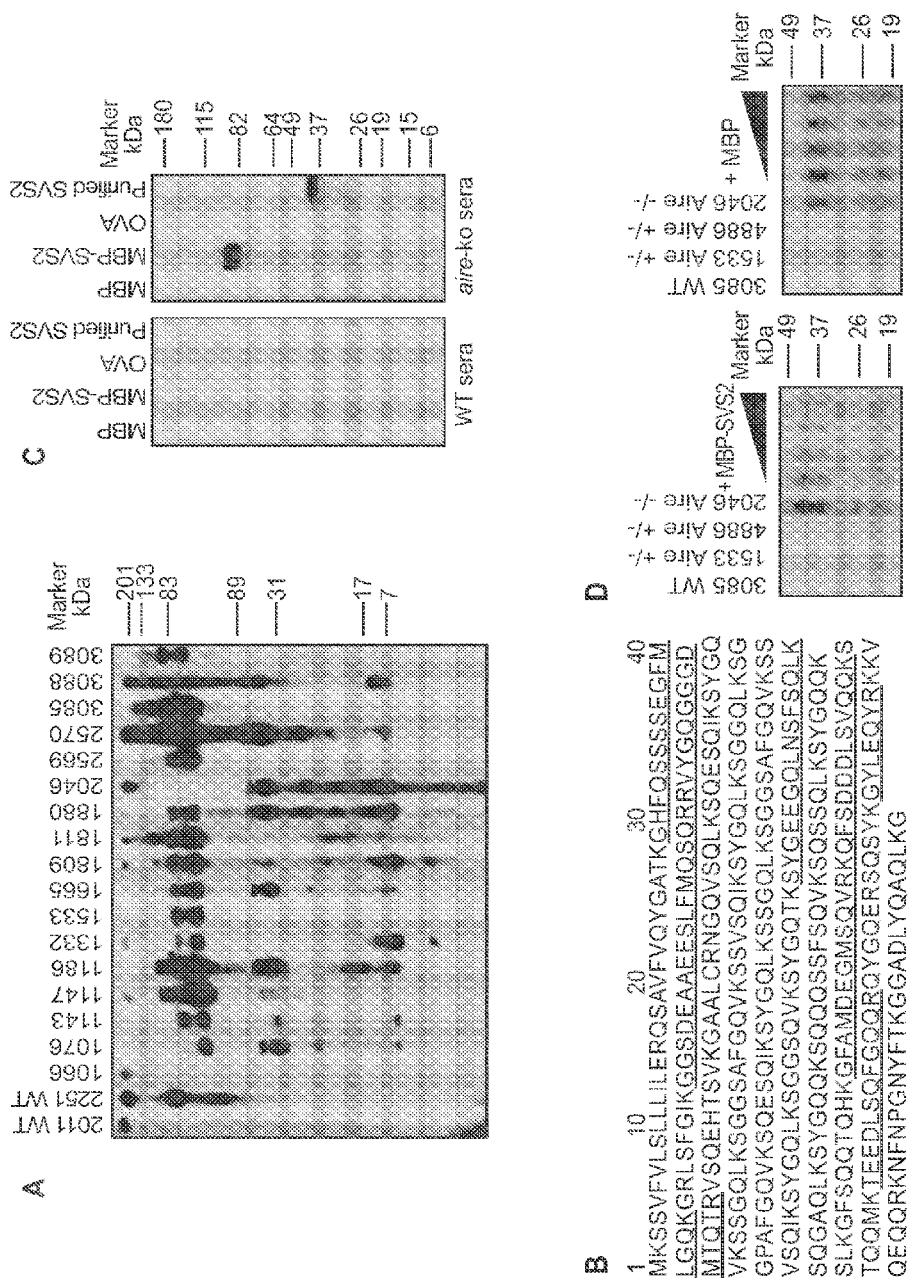
FIGS. 2A-D depict the presence of autoantibodies to SVS2 in Aire-KO mice.
Figure 8:
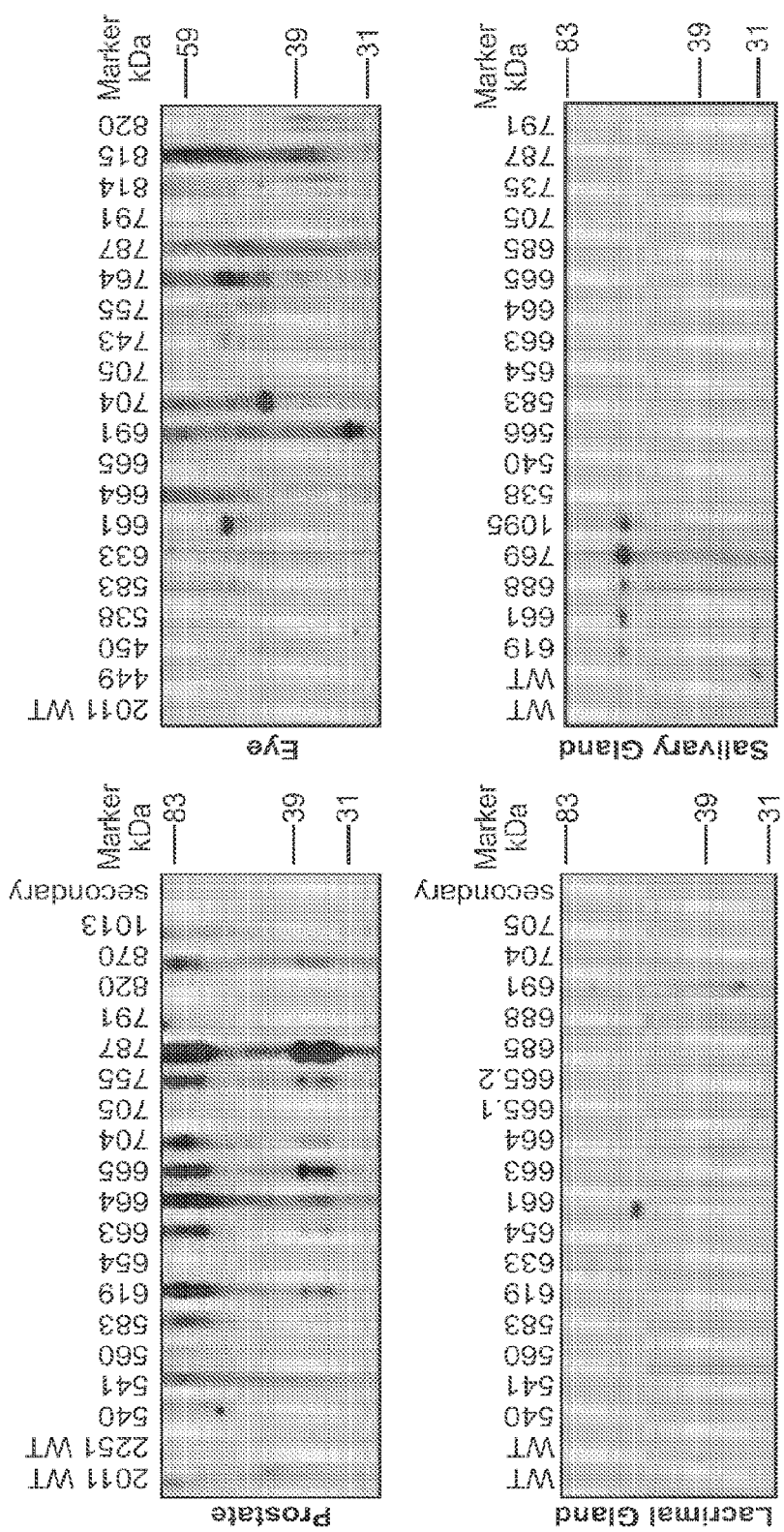
FIG. 8 depicts the presence of prostate-specific autoantibodies in Aire-deficient male mice.

Next, immunoblotting of prostate, eye, lacrimal, and salivary gland extracts were performed with the sera from male Aire-KO and WT mice on the B6/NOD F2 background (individual mice listed by number) (FIG. 8). Each lane of the multi-screen immunoblot represents the reactivity of sera from individual mice. Autoantibodies against prostate-derived proteins could be detected in most Aire-KO sera (FIG. 2A). Some sera showed broad reactivity, whereas others showed more limited and/or weaker reactivity, consistent with heterogeneity in the immune response. Nevertheless, common bands were also evident across multiple mice, indicating that there were immune responses to proteins shared by the majority of the Aire-KO mice. These common bands within the prostate lysate were not evident in immunoblots to lysates from other tissues, such as the eye, salivary, or lacrimal glands, in which Aire-KO mice also develop spontaneous inflammation (FIG. 8).

In an effort to purify and identify the targeted antigens, sera from Aire-KO mice with strong autoreactivity to the lysates and from WT mice were used to make immunoprecipitation columns. These columns were used to enrich for antibody-binding proteins from pooled prostate tissue extracts. Enriched proteins from both Aire-KO and WT sera-coupled columns were concentrated and subjected to gel electrophoresis. Multiple distinct bands that were visualized by silver staining and that were unique to the Aire-KO sera column were excised and analyzed by mass spectroscopy. Seminal vesicle secretory protein 2 (SVS2) was successfully identified with 29% sequence coverage of the protein through peptide mass fingerprinting (PMF) from both the 26 and 38-kD bands. The peptide sequences identified through PMF are denoted in underline and lie predominantly within the N terminus of the SVS2 protein (GenBank Accession No. AAI07277; accession no. 78070545) (FIG. 2B). SVS2 is an androgen-regulated protein expressed by the prostate and secreted into seminal fluid, where it serves as a major clotting protein involved in the formation of the copulatory plug.

To confirm that SVS2 was the protein recognized by autoantibodies in the Aire-KO mice, purified SVS2 was generated through two approaches. Mouse-derived SVS2 protein was purified from the seminal vesicle fluid according to the protocol that was utilized to purify human SG, a protein that has structural similarities to mouse SVS2 protein. This purification procedure yielded the expected 38-kD protein. As an alternative approach, recombinant SVS2 was also produced as an 80-kD fusion protein with maltose binding protein (MBP) expressed in $E.$ $coli$. Recombinant MBP-SVS2 could be purified from bacteria lysate with an amylose column. Recombinant MBP was also expressed and purified from $E.$ $coli$ and used as a control in subsequent experiments.

Sera from Aire-KO mice contained autoantibodies that could recognize both the purified, semen-derived protein and the recombinant protein by western blot (FIG. 2C). Immunoblots of recombinant MBP-SVS2 and purified SVS2 from semen plasma with sera from Aire-KO mice (right) and Aire-sufficient mice (left) on B6×NOD F2 background. MBP and OVA are the negative controls. Aire-KO sera did not bind to the control MBP or another irrelevant protein ovalbumin (OVA). The absence of SVS2 reactivity in the Aire-sufficient sera further supports the importance of Aire regulation in autoreactivity to this antigen.

To confirm that the prostate extract-reactive autoantibodies were specific to SVS2, Aire-KO sera was pre-incubated with varying concentrations MBP-SVS2 fusion protein before immunoblotting the prostate extracts. Anti-SVS2 positive sera from Aire-KO mice were preincubated with either recombinant MBP-SVS2 or MBP control before being used in the immunoblots against the prostate extract. Wild type and B6×NOD F2 Aire-heterozygous sera were used as controls. Increasing concentrations of MBP-SVS2 abrogated immunoreactivity to the bands while pre-incubation with MBP did not alter this immunoreactivity (FIG. 2D). These results indicate that SVS2 is a prostate autoantigen that is targeted by autoantibodies in the Aire-KO mice. Moreover, these results also indicate that some of the recognized lower molecular weight proteins represent fragments of SVS2.

FIGS. 2A-D. Aire-KO Mice Possess Spontaneous Autoantibodies to SVS2.

(A) Immunoblotting of whole prostate extracts was performed with the sera from male Aire-KO and WT mice on the B6/NOD F2 background (individual mice listed by number). Each lane of the multi-screen immunoblot represents the reactivity of sera from individual mice. Gel bands stained by sera from multiple Aire-KO mice were excised and analyzed by mass spectroscopy. (B) Multiple microsequenced peptides were found to be derived from SVS2 (accession no. 78070545). The peptide sequences identified through peptide mass fingerprinting (PMF) are denoted in underline and lie predominantly within the N terminus of the protein. (C) Immunoblots of recombinant MBP-SVS2 and purified SVS2 from semen plasma with sera from Aire-KO mice (right) and -sufficient mice (left) on B6×NOD F2 background. MBP and OVA are the negative controls. (D) Anti-SVS2 positive sera from Aire-KO mice were preincubated with either recombinant MBP-SVS2 or MBP control before being used in the immunoblots against the prostate extract. Wild type and B6×NOD F2 Aire-heterozygous sera were used as controls.

FIG. 8. Aire-Deficient Male Mice Possess Prostate-Specific Autoantibodies.

Immunoblotting of prostate, eye, lacrimal, and salivary gland extracts were performed with the sera from male Aire-KO and WT mice on the B6/NOD F2 background (individual mice listed by number). Each lane of the multi-screen immunoblot represents the reactivity of sera from individual mice. SVS2 Expression in the Thymus is Aire-Dependent.

To elucidate the role Aire plays in central tolerance of self-antigens derived from SVS2, distribution of SVS2 expression was examined as detailed below.

Figure 3:
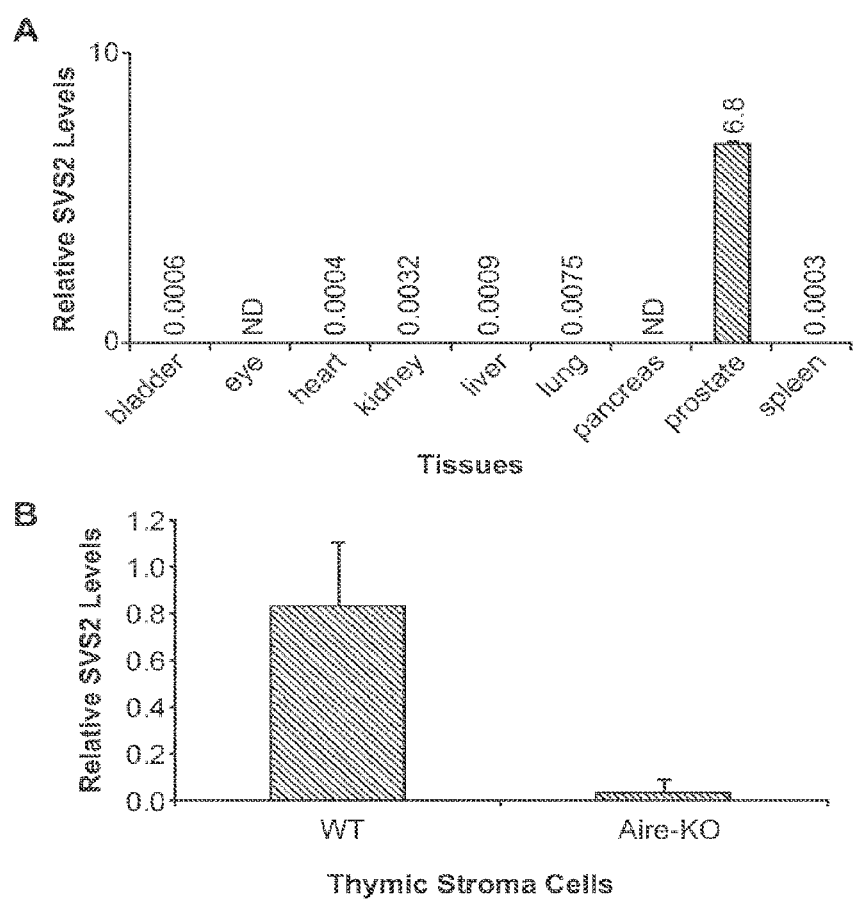
FIGS. 3A and 3B depict the expression profile of SVS2 in various tissues.

To determine the distribution of SVS2 expression, RNA was isolated from different tissues and assessed by real-time PCR to quantify the expression of SVS2 mRNA. Values are normalized to cyclophilin expression for each tissue and are plotted in arbitrary units as denoted. Consistent with prior reports, SVS2 was specifically expressed in the prostate gland but was essentially undetectable in other organs tested, including tissues where spontaneous inflammation can develop in Aire-KO mice (FIG. 3A). As a next step, it is important to determine whether or not SVS2 is expressed in the thymus and whether its thymic expression is Aire-dependent. CD45-negative thymic stromal cells were purified from WT and Aire-KO mice and analyzed the expression of SVS2 by quantitative real-time PCR. Values are normalized to cyclophilin. Results presented are representative of 2 experiments performed. Error bars represent mean±SD. As seen in FIG. 3B, SVS2 was expressed at significant levels in the WT thymus compared to the Aire-KO thymus. This result demonstrates that thymic expression of the SVS2 gene is indeed Aire-dependent.

FIGS. 3A and 3B. SVS2 is Highly Expressed in the Prostate and is an Aire-Dependent Antigen Expressed in the Thymus.

(A). The expression levels of SVS2 were quantitated by RT-PCR on cDNA prepared from diverse tissues. Values are normalized to cyclophilin expression for each tissue and are plotted in arbitrary units as denoted. (B). Quantitative real-time PCR assay for the SVS2 expression in the CD45⁻ thymic stroma cells of Aire-KO and Aire-WT mice. Values are normalized to cyclophilin. Results presented are representative of 2 experiments performed. Error bars represent mean±SD. Autoimmune Prostatitis is Mediated by CD4+ T Cells.

Identifying the immune effectors that participate in the cascade of events leading to prostatitis elucidates the mechanism by which autoimmunity towards prostate proteins is developed.

Figure 4:
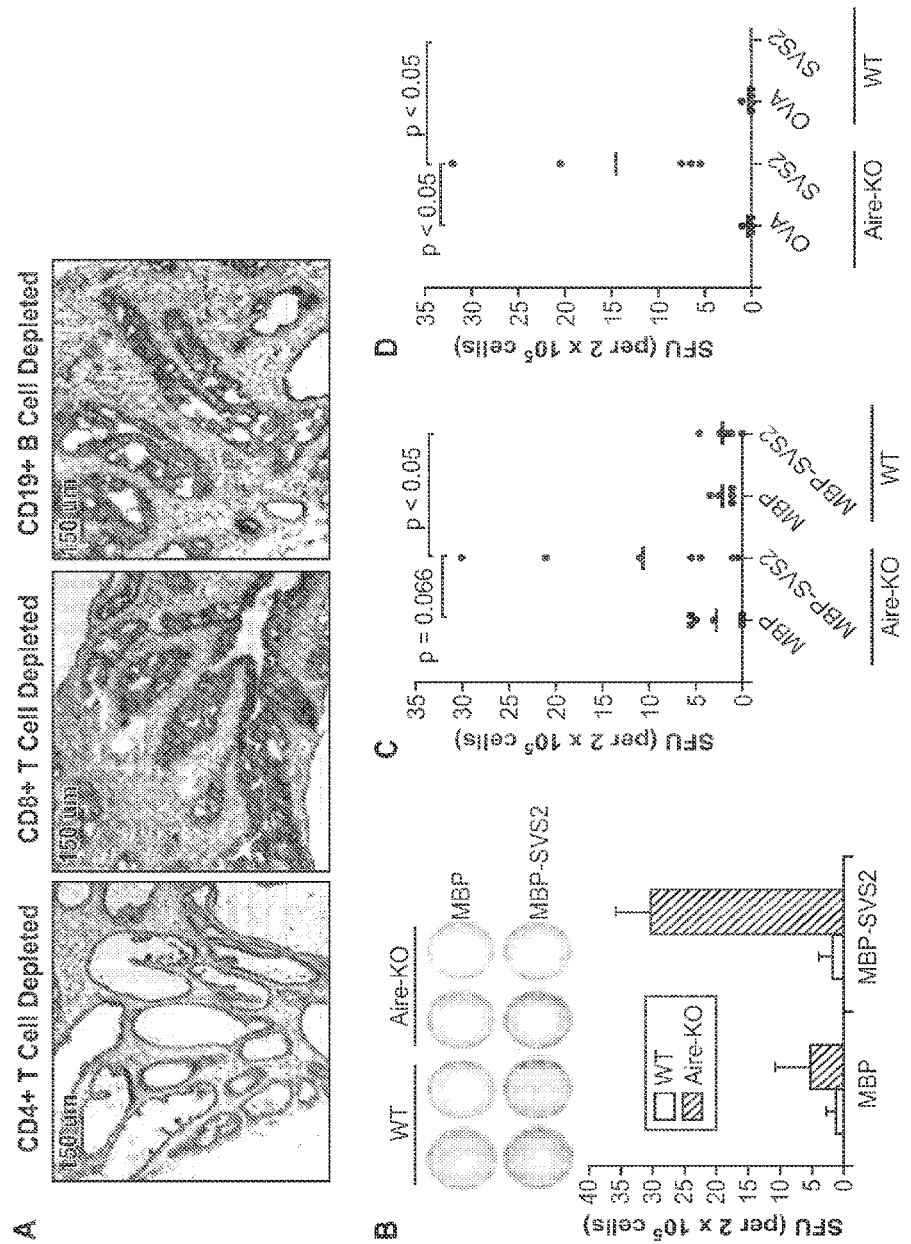
FIGS. 4A-D depict spontaneous T cells responses to SVS2 in Aire-KO mice.

Adoptive transfer experiments were performed to determine the immune effectors that could mediate prostatitis. Splenocytes from Aire-KO B6 mice were pooled, depleted of either CD4+ T cells, CD8+ T cells or CD19+ B cells by FACS, and adoptively transferred into immunodeficient B6/RAG-KO mice. Mice that received CD8+ T cell-depleted (middle panel), or B cell-depleted (right panel) splenocytes developed prostate inflammation with similar pathological characteristics to the Aire-KO mice (FIG. 4A, middle and right panels). Adoptive transfer of CD4+ T cell-depleted splenocytes (left panel), however, failed to induce this level of prostatitis (FIG. 4A, left panel). Results presented are representative of two separate adoptive transfer experiments, each with two mice per group, with magnification of 100×. These results indicate that autoimmune T cells mediate the spontaneous prostatitis seen in Aire-KO mice, of which CD4+ T cells play a dominant role.

Based on these results, it is important to determine whether Aire-KO mice possess SVS2-reactive T cells spontaneously. 200,000 splenocytes per well from Aire-KO mice and WT mice were assessed for T cell responses against MBP-SVS2 (10 mcg/ml) or MBP (10 mcg/ml) by IFN-γ ELISPOT. Through this approach, specific responses could be detected to the MBP-SVS2 fusion protein. While there was heterogeneity in the immune responses to MBP-SVS2 in Aire-KO mice, the responses seen were significantly different from WT mice where no responses to MBP-SVS2 could be detected (FIG. 4B). Aire-KO mice also had higher background reactivity to the control antigen MBP compared to WT mice, so additional mice were assessed for immune responses to non-recombinant, purified proteins. Results from Aire-KO and WT mice are shown (n=7 per group) in FIG. 4C. Mean SFU/group are indicated with dashes with significance assessed by paired Students T-test. Again, spontaneous T cell responses to semen-derived SVS2 were detected only in the Aire-KO mice (FIG. 4C).

IFN-γ ELISPOT assays were also performed with purified semen-derived SVS2 (10 mcg/ml) and OVA (10 mcg/ml) (n=5 per group). Mean SFU/group are again indicated with dashes with significance assessed by two-sided Students T-test (FIG. 4D).

To confirm that SVS2-reactive T cells in fact mediate prostatitis, an SVS2-reactive CD4+ T cell line was generated by stimulating splenocytes from male Aire-KO mice in vitro with purified SVS2. Upon restimulation with SVS2-MBP, the SVS2-reactive T cell line produced IFN-γ, but not IL-17 or IL-10. An ovalbumin (OVA)-reactive T cell line was generated in parallel as a control. Adoptive transfer of the SVS2-reactive T cell line into B6/RAG-KO mice induced prostatitis (pathology score 4) in 3 of 3 treated mice, whereas adoptive transfer of the OVA-specific T cell line resulted in no inflammation.

FIGS. 4A-D. Spontaneous T Cells Responses to SVS2 in Aire-KO Mice.

(A) Splenocytes derived from B6 Aire-KO were depleted of CD4, CD8 T cells or B cells by FACS. $5 \times 10^6$ sorted cells were adoptively transferred into RAG-deficient B6 mice. H&E staining of representative frozen prostate sections indicated that cells depleted of CD8+ T cells (middle), CD19+ B cells (right), but not the CD4+ T cells (left) were capable of transferring disease into RAG-deficient mice. Results presented are representative of two separate adoptive transfer experiments, each with two mice per group. Magnification 100×. (B) 200,000 splenocytes per well from Aire-KO mice and WT mice were assessed for T cell responses against MBP-SVS2 (10 mcg/ml) or MBP (10 mcg/ml) by IFN-γ ELISPOT. (C) Results from Aire-KO and WT mice are shown (n=7 per group). Mean SFU/group are indicated with dashes with significance assessed by paired Students T-test. (D) IFN-γ ELISPOT assays were also performed with purified semen-derived SVS2 (10 mcg/ml) and OVA (10 mcg/ml) (n=5 per group). Mean SFU/group are again indicated with dashes with significance assessed by two-sided Students T-test.

Tolerance to SVS2 can be Broken and Prostatitis can be Induced in Wild-Type B6 Mice.

Based on the results presented above, central tolerance mediated by Aire seems to play a major role in preventing autoimmune prostatitis. In order to further identify the mechanism that resembles human prostatitis, it would be important to determine whether central tolerance to SVS2 is complete in a wild-type setting.

SVS2 was examined for immunogenicity in WT B6 mice by immunizing these mice with recombinant MBP-SVS2. In doing so, whether inducing an immune response to SVS2 is sufficient for triggering prostatitis could also be determined. WT mice were challenged with either MBP-SVS2 (FIG. 5A) or MBP (FIG. 5B) emulsified in complete Freund's adjuvant (CFA). After two booster immunizations with the corresponding protein in incomplete Freund's adjuvant (IFA), sera, splenocytes, and tissues were harvested for analysis. Sera from individual immunized B6 mice were used to immunoblot semen-purified SVS2 or OVA. Each blot represents an individual animal. One group of 4 mice is shown and represents a total of 14 mice that were immunized with MBP-SVS2 or with MBP. To minimize cross-reactivity to potential contaminants in the recombinant antigens, semen-derived SVS2 was used to perform the in vitro assays. Autoantibodies against the semen-derived SVS2 could be detected in the sera of 7 out of 14 mice (FIG. 5A).

Figure 5:
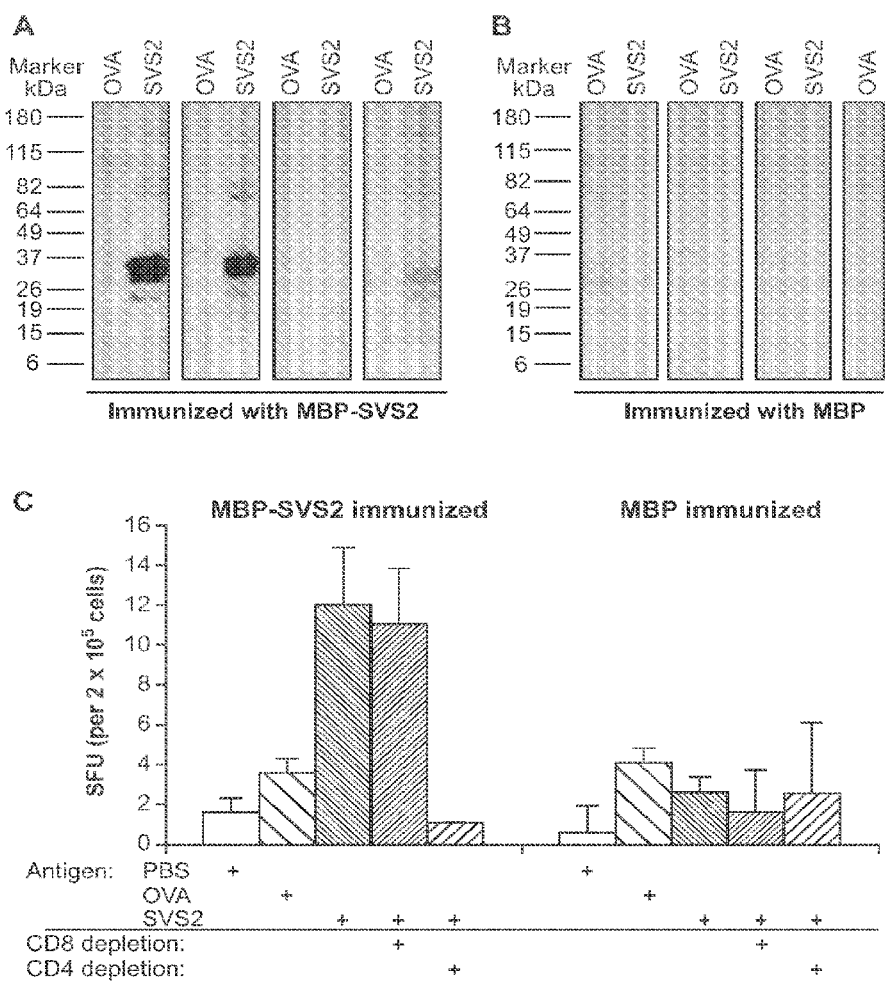
FIGS. 5A-C depict induction of SVS2-specific antibody and T cell response in Aire-sufficient B6 mice.

None of the 14 MBP-immunized mice had any autoantibody activity against SVS2 (FIG. 5B). The pooled splenocytes from 4 mice that were immunized with either the recombinant MBP-SVS2 (left) or MBP (right) were also assessed by IFN-γ ELISPOT for reactivity to purified SVS2 (10 mcg/ml), OVA (10 mcg/ml), or PBS. The splenocytes depleted of CD8+ or CD4+ T cells were also assessed. The splenocytes from MBP-SVS2 immunized mice demonstrated specific reactivity to the semen-derived SVS2, while the splenocytes of MBP immunized mice had no specific immune response against SVS2 (FIG. 5C). Error bars represent mean+SD. Results are representative of two experiments.

Depletion of CD4+ T cells from the MBP-SVS2 immunized splenocytes by FACS sorting eliminated the SVS2-specific response, while depletion of CD8+ T cells had essentially no effect. These results demonstrate that tolerance to this self-antigen can be broken and that both antibody and CD4+ T cell responses can be induced in Aire-sufficient mice.

FIGS. 5A-C. Induction of SVS2-Specific Antibody and T Cell Response by Immunizing Aire-Sufficient B6 Mice with MBP-SVS2.

WT B6 mice were immunized with either (A) MBP-SVS2 or (B) MBP emulsified in CFA. Sera from individual immunized B6 mice were used to immunoblot semen-purified SVS2 or OVA. Each blot represents an individual animal. One group of 4 mice is shown and represents a total of 14 mice that were immunized with MBP-SVS2 or with MBP. (C) The pooled splenocytes from 4 mice that were immunized with either the recombinant MBP-SVS2 (left) or MBP (right) were assessed by IFN-γ ELISPOT for reactivity to purified SVS2 (10 mcg/ml), OVA (10 mcg/ml), or PBS. The splenocytes depleted of CD8+ or CD4+ T cells were also assessed. Error bars represent mean+SD. Results are representative of two experiments.

Next, the prostates of immunized mice were examined for the induction of prostatitis. Male B6 mice were immunized s.c. with the recombinant MBP-SVS2 fusion protein (upper row) or MBP control protein (lower row) emulsified in CFA (FIG. 6A). After two booster immunizations with the respective proteins in IFA, the prostates were analyzed by immunohistochemical staining for CD3+ cells in frozen sections of prostate from the immunized mice with MBP-SVS2 (upper) or MBP (lower). While the severity of inflammation was less than that seen in Aire-KO mice, nevertheless 10 out of 14 MBP-SVS2-immunized mice had intraprostatic CD3+ T cell infiltration (FIG. 6A). These results demonstrate that tolerance to SVS2 can be broken in WT mice with pathologic consequences.

Figure 6:
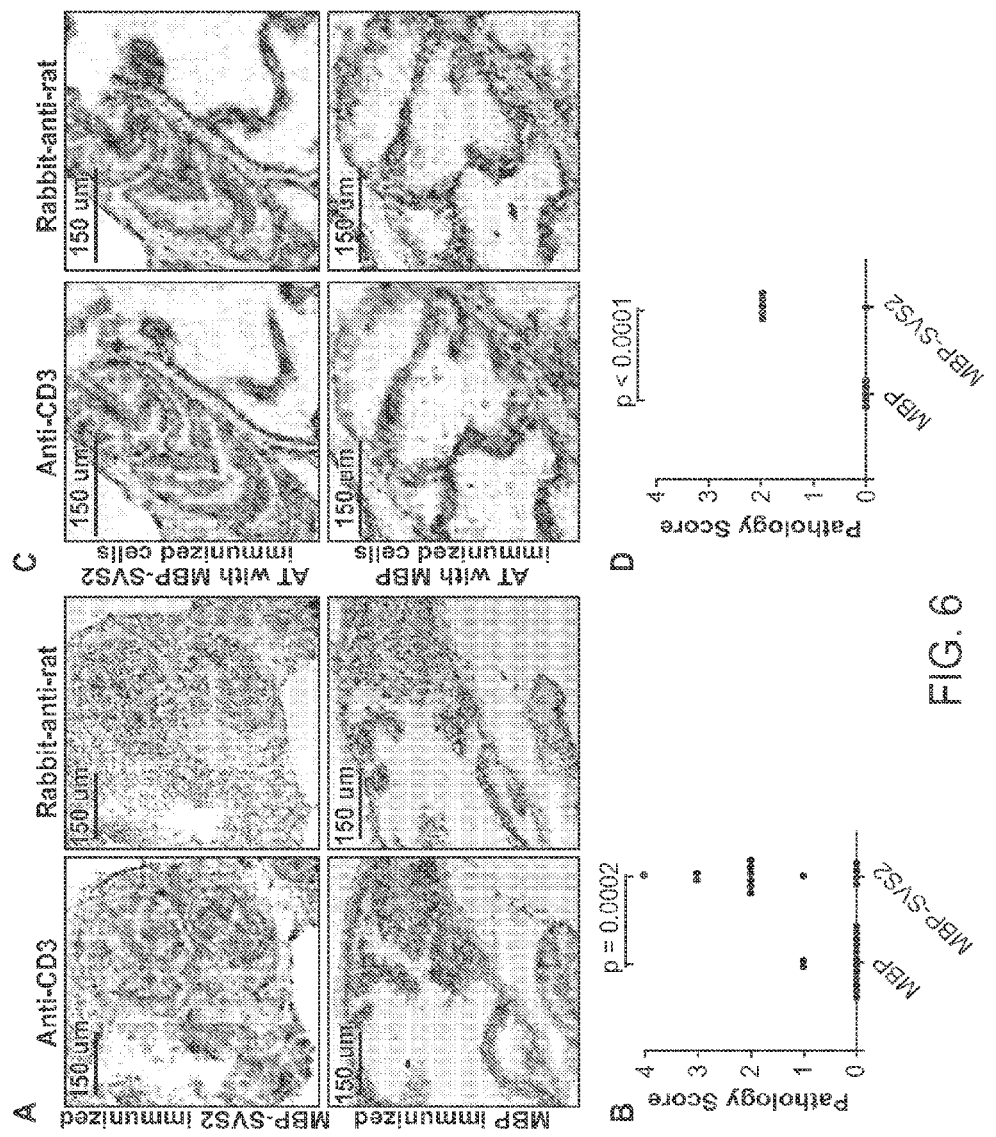
FIGS. 6A-D depicts induction of prostatitis in mice with SVS2 immunization.

To confirm that the induced prostatitis is T cell mediated, adoptive transfer experiments were performed as follows and the results shown in FIG. 6. Pooled splenocytes from the mice that were immunized with MBP-SVS2 (upper row) were adoptively transferred into B6/RAG-KO mice. MBP immunized splenocytes were adoptively transferred into B6/RAG-KO mice as controls (lower row). 4 weeks following transfer, the prostates of recipient mice were assessed for prostatitis. Lymphocyte infiltration in the prostates of each immunized mouse was scored blindly by a pathologist (p<0.005, Students T-test) (FIG. 6B). The intraprostatic CD3+ T cell infiltrates into the glandular epithelium were observed in all mice that received the SVS2-MBP immunized splenocytes (FIG. 6B). None of the mice that received MBP-immunized splenocytes displayed any prostatitis (FIG. 6C). These results further support the role of the T cell response induced by SVS2 in mediating disease.

FIGS. 6A-D. Induction of Prostatitis in Wild-Type B6 Mice with SVS2 Immunization.

(A) Male B6 mice were immunized s.c. with the recombinant MBP-SVS2 fusion protein (upper row) or MBP control protein (lower row) emulsified in CFA. After two booster immunizations with the respective proteins in IFA, the prostates were analyzed by immunohistochemical staining for CD3+ cells in frozen sections of prostate from the immunized mice with MBP-SVS2 (upper) or MBP (lower). (B) Lymphocyte infiltration in the prostates of each immunized mouse was scored blindly by a pathologist. p<0.005, Students T-test. (C) Pooled splenocytes from the mice immunized with the recombinant MBP-SVS2 fusion protein (upper row) or MBP control protein (lower row) were adoptively transferred (AT) i.v. into RAG-deficient mice. 4 weeks later, the prostates were analyzed by immunohistochemical staining for CD3+ cells. (D) Lymphocyte infiltration in the prostates of each mouse was again scored by a pathologist. p<0.005, Students T-test. Chronic Prostatitis Patients Develop Autoimmune Response to Human Semenogelin.

Central tolerance to SVS2 in mice has proven to be crucial in the prevention of autoimmunity leading to prostatitis. As for human prostatitis, the results accumulated from mouse studies presented above may also be applicable. The following experiment demonstrated that T cell immunity against a human semen protein semenogelin is involved in human prostatitis.

While no clear human homologue for SVS2 exists, SVS2 is a member of a family of prostate-specific proteins collective known as "rapidly evolving substrates for transglutaminase" (Lundwall, A., and Lazure, C. (1995) *FEBS Lett* 374:53-56). Similar prostate-specific proteins also exist in humans. Using the same method that was used to purify SVS2 from mouse semen, we purified one such protein, semenogelin (SG), from human semen plasma and examined whether CPPS patients can possess antibodies to this autoantigen. Immunoblotting of purified semenogelin was performed with the sera from CPPS patients (upper panel of FIG. 7A) and age-matched male blood donors (lower panel of FIG. 7A). Each lane of the multi-screen immunoblot represents the reactivity of sera from individual sample. The 52-kDa band represents SG1 and the 71-kDa band represents SG2. Rabbit anti-human semenogelin as a positive control (the 1$^{st}$ lane) and human nonspecific IgG was used as a negative control (the last lane). 15 representative sera were shown from each group.

As expected, the SG preparations contained both isoforms: the 52-kDa SG1 and the 71-kDa SG2. 26 of 39 sera from patients with the clinical diagnosis of CPPS possessed autoantibodies to these proteins (FIG. 7A, top), while only 8 of 39 sera from age-matched normal males possessed these autoantibodies (FIG. 7A, bottom) (Fisher's exact test, two-sided p<0.0001). 16 of the 39 assessed CPPS patients had undergone prostate biopsies as part of their clinical management. 9 of the 16 CPPS patients had prostatitis on biopsy. Interestingly, all patients with biopsy-proven prostatitis had autoantibodies to SG (Table 2).

TABLE 2

Presence of prostatitis biopsy

| Patient ID | Antibody | Prostatitis |
|---|---|---|
| 1109 | + | + |
| 1196 | + | + |
| 1197 | + | + |
| 1229 | + | + |
| 1241 | + | + |
| 1248 | + | + |
| 1261 | + | + |
| 1274 | + | + |
| 1277 | + | + |
| 1218 | + | − |
| 1235 | + | − |
| 1237 | + | − |
| 1259 | + | − |
| 1262 | + | − |
| 1250 | − | − |
| 1256 | − | − |

Figure 7:
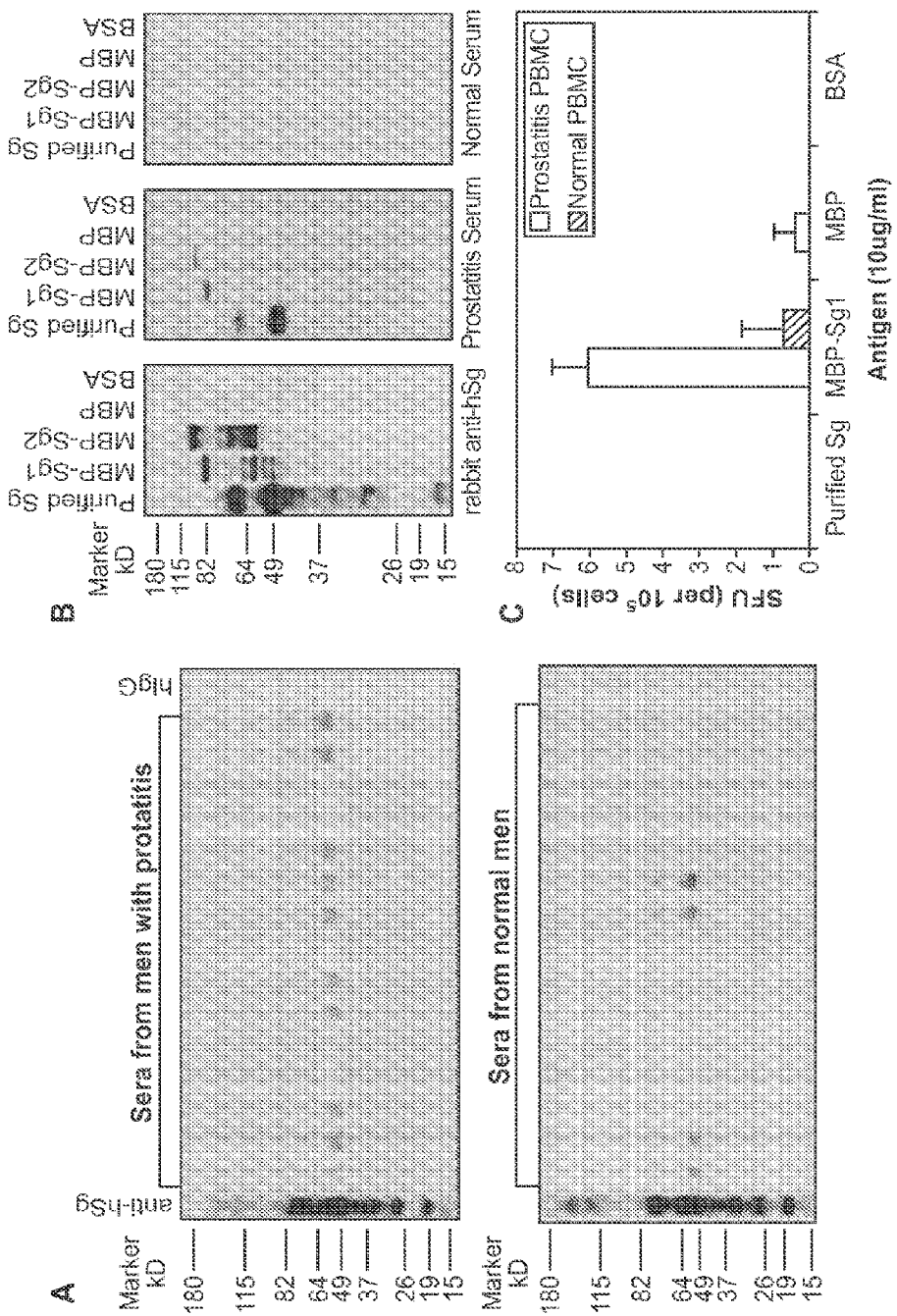
FIGS. 7A-C depict autoimmune response to human semenogelin in prostatitis patients.

The specificity of these autoantibodies was confirmed against recombinant human MBP-SG1- and MBP-SG2 fusion proteins (FIG. 7B). Immunoblots of recombinant MBP-SG1, MBP-SG1 and semenogelin purified from semen plasma are used to detect IgG antibodies within sera from a patient with CPPS (middle) and an age-matched normal male donor (right). Polyclonal rabbit-anti-human semenogelin Ab was used as positive control (left). MBP and BSA represent irrelevant protein controls.

T cell immunity against this antigen could also be detected in the peripheral blood mononuclear cell (PBMC) from a CPPS patient by IFN-γ ELISPOT (FIG. 7C). PBMC from a CPPS patient (opened bar) and an age-matched normal male donor (filled bar) were assessed for T cell responses against the purified semenogelin and MBP-SG1 fusion protein by IFN-γ ELISPOT. 100,000 cells per well were cultured overnight with antigens at 10 µg/ml. The number of spot forming units (SFU) was shown as the mean of triplicate wells.

FIGS. 7A-C. Chronic Prostatitis Patients Possess Autoimmune Response to Human Semenogelin.

(A) Immunoblotting of purified semenogelin was performed with the sera from CPPS patients (upper panel) and age-matched male blood donors (lower panel). Each lane of the multi-screen immunoblot represents the reactivity of sera from individual sample. The 52-kDa band represents Sg1 and the 71-kDa band represents Sg2. Rabbit anti-human semenogelin as a positive control (the 1$^{st}$ lane) and human nonspecific IgG was used as a negative control (the last lane). 15 representative sera were shown from each group. (B)

Immunoblots of recombinant MBP-Sg1, MBP-Sg1, and semenogelin purified from semen plasma were used to detect IgG antibodies within sera from a patient with CPPS (middle) and an age-matched normal male donor (right). Polyclonal rabbit-anti-human semenogelin Ab was used as positive control (left). MBP and BSA represent irrelevant protein controls. (C) PBMC from a CPPS patient (opened bar) and an age-matched normal male donor (filled bar) were assessed for T cell responses against the purified semenogelin and MBP-Sg1 fusion protein by IFN-γ ELISPOT. 100,000 cells per well were cultured overnight with antigens at 10 ug/ml. The number of spot forming units (SFU) was shown as the mean of triplicate wells.

Example 2

Growth of Prostate Cancer Cells in Aire$^{-/-}$ (Knockout) and Wild-Type Mice Five male Aire-KO mice and five wild-type male mice were injected s.c. with Tramp-C2 cells (ATCC number CRL-2731; mouse prostate cancer cell line; $2 \times 10^5$ cells per mouse) on day 0. Tumor growth was monitored every 3 days; the size of the tumor was measured by caliper. When the diameter of the tumor in a given mouse reached 2 cm, mice were sacrificed. All remaining mice were sacrificed on day 67.

Figure 10:
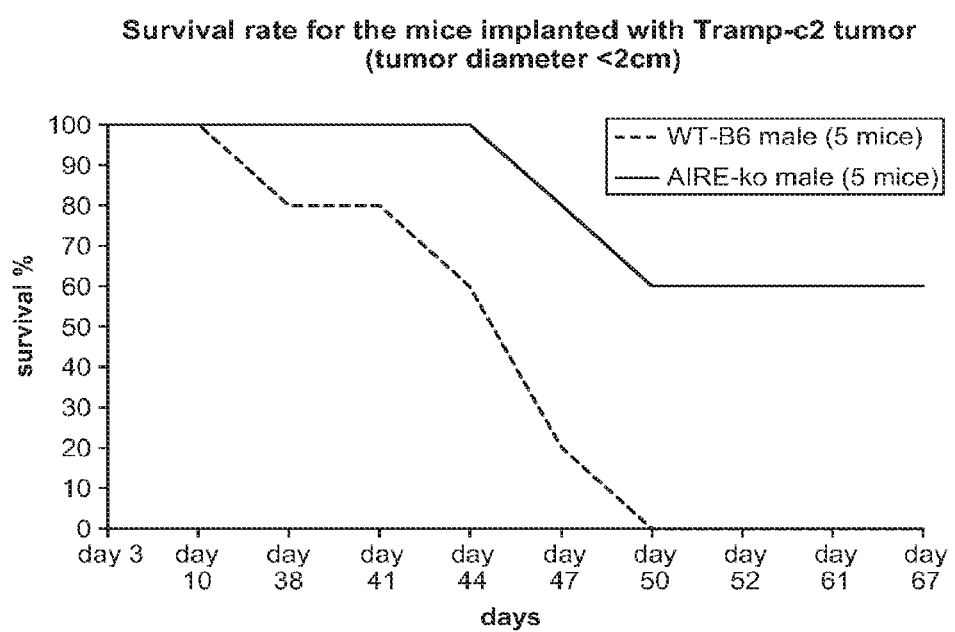
FIG. 10 is a graph depicting survival rates for wild-type (WT-B6) male mice or $Aire^{-/-}$ (AIRE-ko) male mice implanted with Tramp-c2 tumor cells.

The results are shown in FIG. 10. As shown in FIG. 10, the survival rate for Aire-KO mice was much higher than that for wild-type mice. Thus, prostate cancer cells grow more slowly in Aire-KO mice than in wild-type mice.

Example 3

Expression of PAA in BPH and Prostate Cancer

Figure 11:
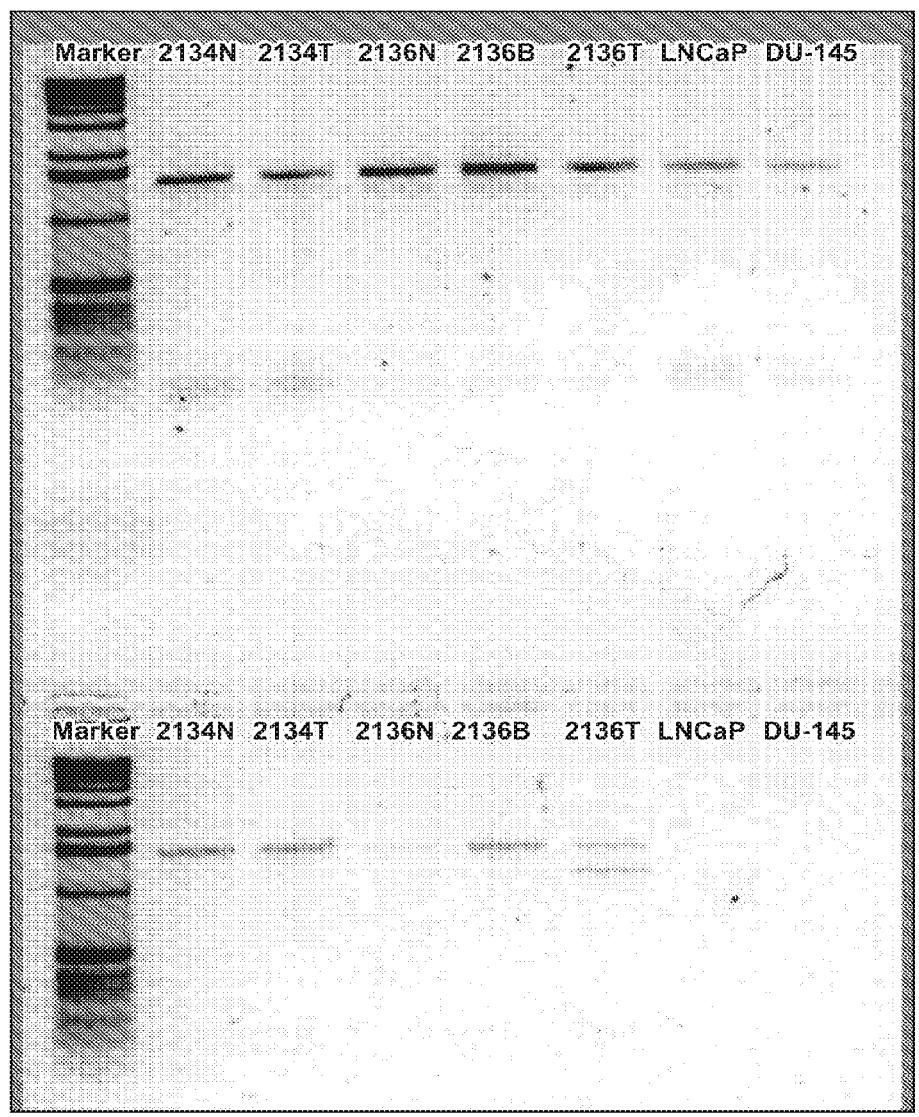
FIG. 11 depicts expression of Sgl1 and Sgl2 in human BPH and prostate cancer cells.

Reverse transcription-polymerase chain reaction (RT-PCR) was performed on RNA obtained from prostate tissue of 2 human male prostate cancer patients undergoing radical prostatectomy (patient identifiers 2134 and 2136). Prostate tissues were dissected into normal prostate (N), BPH (B), and tumors (T). RNA was also prepared from 2 prostate cancer cell lines (LNCap; and DU-145). RT-PCR was performed using primers specific for Sg1 (upper panel) and primers specific for Sg2 (lower panel). The results, shown in FIG. 11, indicate that BPH and prostate cancer cells express Sg11 and Sg12.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of diagnosing an individual as having prostatitis, the method comprising:
   assaying the level of T cells specific for a human semenogelin polypeptide in a biological sample obtained from the individual;
   identifying the individual as having prostatitis when the level of T cells specific for the human semenogelin polypeptide is greater than a normal control level; and
   outputting a report indicating the level of T cells specific for the human semenogelin polypeptide.

2. The method of claim 1, wherein said biological sample is serum, blood, plasma, or seminal fluid.

3. The method of claim 1, wherein said individual is a human male.

4. The method of claim 1, wherein said individual has a higher than normal level of prostate-specific antigen.

5. The method of claim 1, further comprising assaying the level of prostate specific antigen (PSA) in the biological sample, wherein the level of PSA provides for diagnosis of prostate cancer.

* * * * *